(12) United States Patent
Kobayashi et al.

(10) Patent No.: US 9,376,459 B2
(45) Date of Patent: Jun. 28, 2016

(54) TRIARYLPHOSPHINE OR TRIARYLARSINE COMPOUND, ALPHA-OLEFIN POLYMERIZATION CATALYST USING THE COMPOUND, TERNARY COPOLYMER, AND PRODUCTION PROCESS OF ALPHA-OLEFIN-((METH)ACRYLIC ACID)-BASED COPOLYMER

(75) Inventors: Minoru Kobayashi, Yokkaichi (JP);
Hideshi Uchino, Yokkaichi (JP);
Kazuhiro Yamamoto, Kawasaki (JP)

(73) Assignees: Japan Polyethylene Corporation, Tokyo (JP); Japan Polypropylene Corporation, Tokyo (JP)

( * ) Notice: Subject to any disclaimer, the term of this patent is extended or adjusted under 35 U.S.C. 154(b) by 417 days.

(21) Appl. No.: 13/130,494

(22) PCT Filed: Nov. 20, 2009

(86) PCT No.: PCT/JP2009/069740
§ 371 (c)(1),
(2), (4) Date: Jun. 2, 2011

(87) PCT Pub. No.: WO2010/058849
PCT Pub. Date: May 27, 2010

(65) Prior Publication Data
US 2011/0257351 A1   Oct. 20, 2011

(30) Foreign Application Priority Data

Nov. 20, 2008 (JP) .................. 2008-297411
Feb. 5, 2009 (JP) .................. 2009-025443

(51) Int. Cl.
| | |
|---|---|
| *B01J 31/00* | (2006.01) |
| *C08F 4/80* | (2006.01) |
| *C08F 4/44* | (2006.01) |
| *C08F 4/06* | (2006.01) |
| *C07F 15/04* | (2006.01) |
| *C07F 9/50* | (2006.01) |
| *C07F 9/655* | (2006.01) |
| *C07F 9/74* | (2006.01) |
| *C08F 10/00* | (2006.01) |
| *C08F 210/16* | (2006.01) |

(52) U.S. Cl.
CPC .............. *C07F 15/04* (2013.01); *C07F 9/5022* (2013.01); *C07F 9/65515* (2013.01); *C07F 9/74* (2013.01); *C08F 10/00* (2013.01); *C08F 210/16* (2013.01)

(58) Field of Classification Search
CPC .............. C08F 4/06; C08F 4/44; C08F 4/80; B01J 31/00
USPC .......... 502/162, 168, 217, 155; 526/139, 145, 526/171
See application file for complete search history.

(56) References Cited

U.S. PATENT DOCUMENTS

| | | | |
|---|---|---|---|
| 5,698,651 A | 12/1997 | Kawasaki et al. | |
| 2002/0099155 A1 | 7/2002 | Inoue et al. | |
| 2003/0144441 A1 | 7/2003 | Sen et al. | |
| 2006/0063898 A1 | 3/2006 | Inoue et al. | |
| 2007/0049712 A1* | 3/2007 | Allen ................. | C08F 210/02 526/171 |

(Continued)

FOREIGN PATENT DOCUMENTS

| | | |
|---|---|---|
| CN | 1139676 A | 1/1997 |
| CN | 1769313 A | 5/2006 |
| CN | 1923859 A | 3/2007 |

(Continued)

OTHER PUBLICATIONS

Stefan Mecking, et al., "Mechanistic Studies of the Palladium-Catalyzed Copolymerization of Ethylene and α-Olefins with Methyl Acrylate", J. Am. Chem. Soc., vol. 120, No. 5, Jan. 27, 1998, pp. 888-899.

(Continued)

*Primary Examiner* — Alexa Neckel
*Assistant Examiner* — Elizabeth Eng
(74) *Attorney, Agent, or Firm* — Oblon, McClelland, Maier & Neustadt, L.L.P.

(57) ABSTRACT

To provide an industrially useful α-olefin.((meth)acrylic acid)-based olefin copolymer having both a high molecular weight and a high comonomer content, a catalyst component capable of realizing a production of two different kinds of α-olefin.((meth)acrylic acid)-based olefin copolymers, and a production process using the catalyst. An α-olefin.((meth)acrylic acid)-based olefin copolymer is produced by using a metal complex complexed with a ligand represented by the following formula (Y is phosphorus or arsenic) for a catalyst composition.

[Chem. 1]

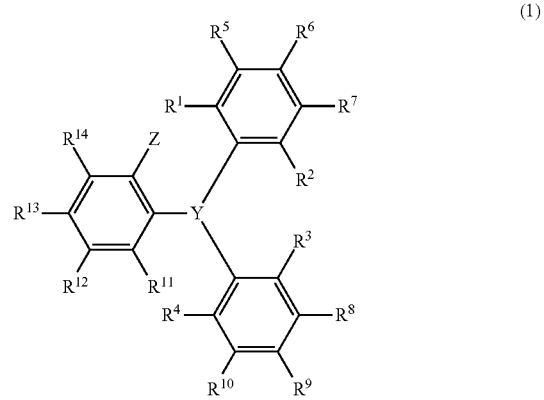

(1)

7 Claims, No Drawings

(56) References Cited

U.S. PATENT DOCUMENTS

2008/0207854 A1    8/2008  Conner et al.
2009/0326174 A1*  12/2009  Scott et al. .................... 526/130

FOREIGN PATENT DOCUMENTS

| JP | 1-282204 | 11/1989 |
| JP | 2000-319332 | 11/2000 |
| JP | 2001-231149 | 8/2001 |
| JP | 2002-80515 | 3/2002 |
| JP | 2002-521534 | 7/2002 |
| JP | 2007-46032 | 2/2007 |
| JP | 2007-63280 | 3/2007 |
| JP | 2007-77395 | 3/2007 |
| JP | 2007-117991 | 5/2007 |
| JP | 2007-214629 | 8/2007 |
| JP | 2007-214630 | 8/2007 |
| JP | 2008-214628 | 9/2008 |
| JP | 2008-214629 A | 9/2008 |
| JP | 2008-214630 A | 9/2008 |
| JP | 2008-223011 A | 9/2008 |
| WO | WO 00/06615 A1 | 2/2000 |
| WO | WO 03/042254 A1 | 5/2003 |

OTHER PUBLICATIONS

Eite Drent, et al., "Palladium catalysed copolymerisation of ethene with alkylacrylates: polar comonomer built into the linear polymer chain", Chem. Commun. 2002, pp. 744-745.

Takuya Kochi, et al., "Synthesis of anionic methylpalladium complexes with phosphine—sulfonate ligands and their activities for olefin polymerization", Dalton Transactions, 2006, pp. 25-27.

W. Keim, "Chelate Complexes of Nickel: Catalysts for the Oligomerization/Poly-Merization of Ethylene", Stud. Surf. Sci. Catal., 25, 1986, pp. 201-213.

Kirill M. Skupov, et al., "Palladium Aryl Sulfonate Phosphine Catalysts for the Copolymerization of Acrylates with Ethene", Macromolecular Rapid Communications, vol. 28, 2007, pp. 2033-2038.

Javier Vela, et al., Ethylene Polymerization by Palladium Alkyl Complexes Containing Bis(aryl)phosphino-toluenesulfonate Ligands, Organometallics, vol. 26, No. 26, Nov. 21, 2007, 1 front page, pp. 6624-6635.

Alicja Haras, et al., "Comparative Study on Catalytic Systems for the Alternating and Nonalternating CO/Ethene Copolymerization", Organometallics, vol. 25, No. 4, Jan. 17, 2006, pp. 946-953.

Shengsheng Liu, et al, "Copper-Mediated Controlled Copolymerization of Methyl Acrylate with 1-Alkenes under Mild Conditions", J. Am. Chem. Soc., vol. 123, No. 50, Nov. 17, 2001, pp. 12738-12739.

International Search Report issued Feb. 16, 2010, in PCT/JP2009/069740.

Office Action issued May 31, 2013, in Chinese Patent Application No. 200980155043.4 with English translation.

Office Action issued Dec. 3, 2013 in Japanese Patent Application No. 2010-024896 with English language translation.

Office Action issued Apr. 7, 2016 in Chinese Patent Application No. 201410395297.6 filed Nov. 20, 2009 w/partial English translation.

* cited by examiner

TRIARYLPHOSPHINE OR TRIARYLARSINE COMPOUND, ALPHA-OLEFIN POLYMERIZATION CATALYST USING THE COMPOUND, TERNARY COPOLYMER, AND PRODUCTION PROCESS OF ALPHA-OLEFIN-((METH)ACRYLIC ACID)-BASED COPOLYMER

TECHNICAL FIELD

The present invention relates to a novel triarylphosphine or triarylarsine compound, an α-olefin polymerization catalyst using the compound, and a production process of an α-olefin. ((meth)acrylic acid)-based copolymer. More specifically, the present invention relates to an α-olefin.((meth)acrylic acid)-based ternary copolymer having both a high molecular weight and a high comonomer content, and a production process thereof, which are realized by virtue of an α-olefin-based polymerization catalyst using the novel compound above.

BACKGROUND ART

Out of resin materials, an ethylene polymer and an ethylene-based polymer such as copolymer of an ethylene and an α-olefin are excellent in the physical properties or various properties such as moldability and have a superiority in view of profitability, environmental compliance and the like, and these materials have been heretofore very widely employed for general purposes and are being used as an important industrial material. However, the ethylene-based polymer has no polar group and its application to the field requiring physical properties such as adhesion to another material, printing suitability or compatibility, for example, with a filler is limited. In the application where physical properties such as adhesion to another material, printing suitability or compatibility, for example, with a filler are required, a copolymer of an ethylene and a polar group-containing vinyl monomer, produced by a high-pressure radical polymerization process, has been used by itself or as a composition with another resin. However, the polar group-containing ethylene-based polymer produced by high-pressure radical polymerization can be only a low-modulus material and is poor also in the mechanical properties, and its application particularly to a field requiring high strength is limited even when used as a composition with another resin as well as when used by itself.

Since the 1990s, polar group-containing comonomer copolymerization using a late transition metal complex catalyst has been aggressively studied, and there are known, for example, an (α-diimine)palladium complex reported by Brookhart et al., a (salicylamidinato)nickel catalyst reported by Grubbs et al., and a (phosphanylphenolato)nickel catalyst called a SHOP catalyst. In use of such a catalyst, the polymerization temperature is set to be relatively low so as to suppress a frequent occurrence of chain transfer, and the productivity of the copolymer as well as its molecular weight are generally low (see, for example, Non-Patent Document 1).

In 2002, Pugh et al. have reported that when a phosphine sulfonate ligand is combined with a palladium compound and used as a catalyst component, copolymerization even at a high temperature (80° C.) can be performed (see, Patent Document 1 and Non-Patent Document 2), and this technique enables realizing high productivity and moreover, ensures a relatively high content of a (meth)acrylic ester as a comonomer. However, the molecular weight (Mw) of the copolymer obtained has an upper limit of about tens of thousands and therefore, industrial application of this copolymer is also limited.

The phosphine sulfonate ligand above is estimated to be a chelating or potentially chelating ligand and has been reported, for example, to become a chelated metal complex by complexing with palladium (Non-Patent Document 3). Also, it has been reported that a phosphine carboxylate ligand having a —$CO_2H$ group becomes a chelated metal complex by complexing with nickel (Non-Patent Document 4).

Nozaki et al. have reported that a (phosphine-sulfonato) palladium (methyl)lutidine complex is isolated as a catalytically active component and this is useful as a catalyst (see, Patent Document 2 and Non-Patent Document 3). In this case, the catalytic activity is greatly enhanced, but the molecular weight still remains low.

Ethylene polymerization and ethylene/1-hexene copolymerization each using the isolated (phosphine sulfonato)palladium (methyl)lutidine complex have been reported by Jordan et al. (Non-Patent Document 6). The report says that this catalyst does not absorb 1-hexene in the case of polymerization under an ethylene pressure (3 MPa) but copolymerizes a slight amount of hexene in the case of a low ethylene pressure (0.5 MPa).

Goodall et al. have developed a phosphine sulfonate ligand having a biphenyl structure by improving the phosphine sulfonate ligand (see, for example, Patent Documents 3 to 8 and Non-Patent Document 5). It is disclosed that by using this ligand as a catalyst for the copolymerization of an ethylene and an acrylic ester, a copolymer having a molecular weight (Mw) of 100,000 or more can be produced. However, according to the evaluation by the present inventors, it has been found that the comonomer content disadvantageously decreases.

Accordingly, in the field of copolymerization of an ethylene and a vinyl acetate as a polar group-containing vinyl monomer or a ((meth)acrylic acid)-based olefin, development of a polymerization catalyst capable of satisfying both high copolymerizability and high molecular weight (Mw) is being demanded.

On the other hand, a ternary copolymer of an ethylene, an α-olefin and a polar group-containing monomer is also known and, for example, an ethylene.1-octene.ethyl acrylate ternary copolymer having an ethyl acrylate content of 12.1 to 35.5 mol % and being produced using a specific chromium-based catalyst is disclosed in Patent Document 9. However, this polymer is yet insufficient in view of improving the balance between the mechanical properties and the adhesion and moreover, it still leaves problems such as many sticky components, generation of die lip build up at the molding, and film blocking. Also, Patent Document 10 discloses an ethylene.propylene.methyl acrylate ternary copolymer having a propylene content of 13.5 to 18.5 mol % and a methyl acrylate content of 8 to 27.2 mol % and being produced using a specific vanadium-based catalyst, but the studies by the present inventors have revealed that the strength of the polymer obtained is below the level expected of a polyethylene as a material. In this way, compared with an ethylene-based (co)polymer containing no polar group, great reduction in the mechanical properties of an ethylene-based copolymer containing a polar group is inevitable.

RELATED ART

Patent Document
    Patent Document 1: JP-T-2002-521534 (the term "JP-T" as used herein means a published Japanese translation of a PCT patent application)
    Patent Document 2: JP-A-2007-46032 (the term "JP-A" as used herein means an "unexamined published Japanese patent application")
    Patent Document 3: JP-A-2007-63280
    Patent Document 4: JP-A-2007-77395
    Patent Document 5: JP-A-2007-117991
    Patent Document 6: JP-A-2008-214628
    Patent Document 7: JP-A-2007-214629
    Patent Document 8: JP-A-2007-214630
    Patent Document 9: JP-A-1-282204
    Patent Document 10: JP-A-2000-319332
Non-Patent Document
    Non-Patent Document 1: S. Mecking et al., *J. Am. Chem. Soc.*, 1998, 120, 888.
    Non-Patent Document 2: E. Drent et al., *Chem. Commun.*, 2002, 744.
    Non-Patent Document 3: K. Nozaki et al., *Dalton TRANSACTIONS*, 2006, 25.
    Non-Patent Document 4: W. Keim, *Stud. Surf. Sci. Catal.*, 1986, 25, 201.
    Non-Patent Document 5: J. P. Clayerie et al., *Macromolecular Rapid Communications*, 2007, 28, 2033-2038
    Non-Patent Document 6: R. F. Jordan et al., *Organometallics*, 2007, 26, 6624-35.

SUMMARY OF THE INVENTION

Problems that the Invention is to Solve

Under these circumstances of the background art, the present invention provides an industrially useful α-olefin.((meth)acrylic acid)-based copolymer having both a high molecular weight and a high comonomer content, a catalyst component capable of realizing the production of two different kinds of α-olefin.((meth)acrylic acid)-based copolymers, and a production process of the copolymer using the catalyst.

Also, the present invention provides an α-olefin.((meth)acrylic acid)-based ternary copolymer having a very narrow molecular weight distribution in a specific range and having a melting point in a specific range.

Means for Solving the Problems

In order to solve the above-described problems, the present inventors have intended to develop a polymerization catalyst capable of realizing the production of an α-olefin.((meth)acrylic acid)-based olefin copolymer having both a high molecular weight an a high comonomer content and have made various investigations of a ligand compound in a late transition metal complex catalyst, as a result, it has been found that novel triarylphosphine and triarylarsine compounds remarkably function as a polymerization catalyst component meeting the above-described purpose. The present invention has been realized based on this finding.

These triarylphosphine and triarylarsine compounds having a specific structure are a novel compound constituting a first invention of the present invention, that is, a triarylphosphine or triarylarsine compound represented by the following formula (1). (Incidentally, the term "the present invention" means the invention group consisting of respective invention units of the following first to twentieth inventions.)

[Chem. 1]

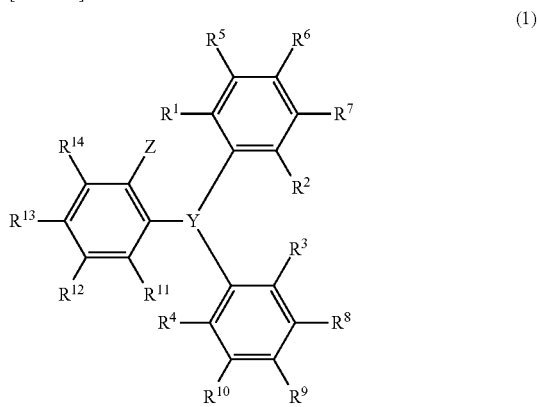

(wherein Y is phosphorus or arsenic, Z is —SO$_3$H or CO$_2$H, each of R$^1$ to R$^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, at least one of R$^1$ to R$^4$ is a substituent where the carbon directly bonded to the aromatic ring is single-bonded to two or more elements selected from the group consisting of C, O and N, and each of R$^5$ to R$^{14}$ independently represents a hydrogen atom, a halogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, an aryloxy group having a carbon number of 6 to 30, or a silyl group substituted with a hydrocarbon group having a carbon number of 1 to 30).

As a second invention, the present invention provides the novel triarylphosphine or triarylarsine compound, wherein in formula (1), each of R$^1$ to R$^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30 and at least one of R$^1$ to R$^4$ is a secondary or tertiary alkyl group.

As a third invention, the present invention provides a novel triarylphosphine or triarylarsine compound represented by the following formula (1):

[Chem. 2]

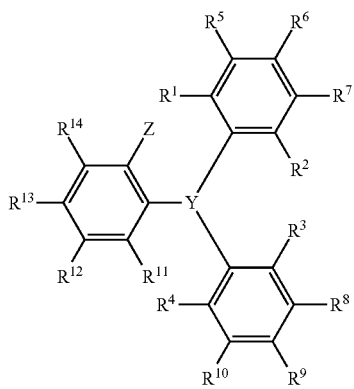
(1)

(wherein Y is phosphorus or arsenic, Z is —SO$_3$H or CO$_2$H, each of $R^1$ to $R^4$ independently represents a hydrogen atom or a hydrocarbon group having a carbon number of 1 to 30, which may have a heteroatom, at least one of $R^1$ to $R^4$ is a secondary or tertiary alkyl group, and each of $R^5$ to $R^{14}$ independently represents a hydrogen atom, a halogen atom, or a hydrocarbon group having a carbon number of 1 to 30, which may have a heteroatom).

As a fourth invention, the present invention provides the novel triarylphosphine or triarylarsine compound, wherein in formula (1) at least one of $R^1$ and $R^2$ and at least one of $R^3$ and $R^4$ are a secondary or tertiary alkyl group.

As a fifth invention, the present invention provides an α-olefin polymerization catalyst obtained by reacting the compound above and a Group 8-10 transition metal compound.

As a sixth invention, the present invention provides an α-olefin polymerization catalyst comprising the compound above, a Group 8-10 transition metal compound and a fine particle support.

As a seventh invention, the present invention provides a metal complex represented by the following formula (2):

[Chem. 3]

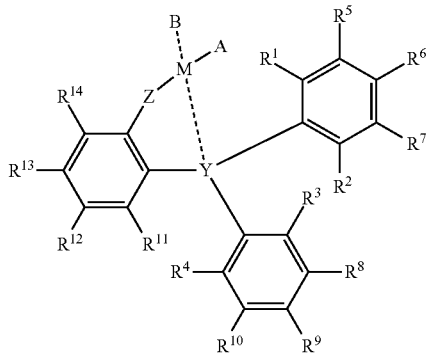
(2)

(wherein Y is phosphorus or arsenic, Z is —SO$_3$— or CO$_2$—, each of $R^1$ to $R^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, at least one of $R^1$ to $R^4$ is a substituent where the carbon directly bonded to the aromatic ring is single-bonded to two or more elements selected from the group consisting of C, O and N, each of $R^5$ to $R^{14}$ independently represents a hydrogen atom, a halogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, an aryloxy group having a carbon number of 6 to 30, or a silyl group substituted with a hydrocarbon group having a carbon number of 1 to 30, M represents a metal atom selected from the group consisting of transition metals of Groups 8 to 10, A represents a hydrogen atom, a halogen atom, an alkyl group having a carbon number of 1 to 30, which may have a heteroatom, or an aryl group having a carbon number of 6 to 30, which may have a heteroatom, B represents an arbitrary ligand coordinated to M, and A and B may combine with each other to form a ring).

As an eighth invention, the present invention provides the metal complex, wherein in formula (2), each of $R^1$ to $R^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, and at least one of $R^1$ to $R^4$ is a secondary or tertiary alkyl group.

As a ninth invention, the present invention provides a metal complex represented by the following formula (2):

[Chem. 4]

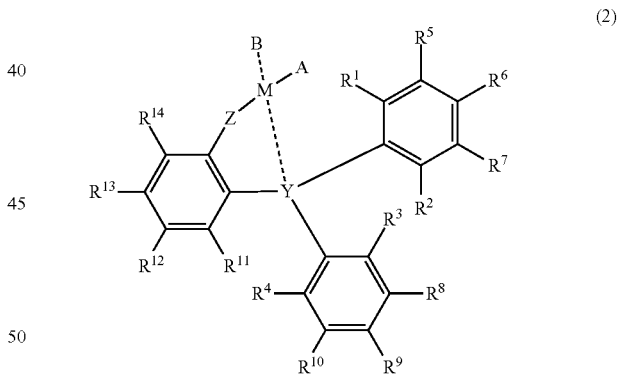
(2)

(wherein Y is phosphorus or arsenic, Z is —SO$_3$— or CO$_2$—, each of $R^1$ to $R^4$ independently represents a hydrogen atom or a hydrocarbon group having a carbon number of 1 to 30, which may have a heteroatom, at least one of $R^1$ to $R^4$ is a secondary or tertiary alkyl group, each of $R^5$ to $R^{14}$ independently represents a hydrogen atom, a halogen atom, or a hydrocarbon group having a carbon number of 1 to 30, which may have a heteroatom, M represents a metal atom selected from the group consisting of transition metals of Groups 8 to 10, A represents a hydrogen atom, an alkyl group having a carbon number of 1 to 30, which may have a heteroatom, or an aryl group having a carbon number of 6 to 30, which may have a heteroatom, B represents an arbitrary ligand coordinated to M, and A and B may combine with each other to form a ring).

As a tenth invention, the present invention provides the metal complex, wherein in formula (2), at least one of $R^1$ and $R^2$ and at least one of $R^3$ and $R^4$ are a secondary or tertiary alkyl group.

As an eleventh invention, the present invention provides an α-olefin polymerization catalyst comprising the metal complex above.

As a twelfth invention, the present invention provides an α-olefin polymerization catalyst comprising the metal complex above and a fine particle support.

As a thirteenth invention, the present invention provides the α-olefin polymerization catalyst, wherein the fine particle support is an ion-exchanging layered silicate.

As a fourteenth invention, the present invention provides the α-olefin polymerization catalyst, wherein the ion-exchanging layered silicate belongs to a smectite group.

As a fifteenth invention, the present invention provides a process for producing an α-olefin.((meth)acrylic acid)-based copolymer, comprising copolymerizing an α-olefin and a (meth)acrylic acid or ester in the presence of the α-olefin polymerization catalyst above.

As a sixteenth invention, the present invention provides a process for producing an α-olefin.((meth)acrylic acid)-based copolymer, comprising copolymerizing three components: two different kinds of α-olefins; and a (meth)acrylic acid or ester, in the presence of the α-olefin polymerization catalyst above.

As a seventeenth invention, the present invention provides a ternary copolymer of an ethylene, an α-olefin having a carbon number of 3 to 10 and a (meth)acrylic acid or ester represented by $CH_2=C(R^{18})CO_2(R^{19})$ (wherein $R^{18}$ is a hydrogen atom or an alkyl group having a carbon number of 1 to 10, and $R^{19}$ is a hydrogen atom or an alkyl group having a carbon number of 1 to 30, which may contain a hydroxyl group, an alkoxy group or an epoxy group on an arbitrary position), the ternary copolymer satisfying the following requirements (a) and (b):

(a) the ratio Mw/Mn of the weight average molecular weight (Mw) to the number average molecular weight (Mn) satisfies the following relationship:

$$1.5 \leq Mw/Mn \leq 3$$

(b) the melting point Tm (° C.), the α-olefin content [C] (mol %) and the polar group-containing vinyl monomer content [X] (mol %) satisfy the following relationship:

$$60 \leq Tm \leq 135 - 6.4 \times ([C]+[X])$$

wherein Tm is a peak temperature of a melting curve obtained by the measurement using a differential scanning calorimeter (DSC) and when a plurality of melting peaks are detected, Tm is the temperature of the maximum peak out of detected peaks.

As an eighteenth invention, the present invention provides the ternary copolymer above, wherein a phase angle δ(G*=0.1 MPa) at G*=0.1 MPa as measured by a rotary rheometer is from 40 to 75°.

As a nineteenth invention, the present invention provides the ternary copolymer above, wherein a difference T90–T10 (° C.) between a temperature T10 (° C.) allowing 10 wt % of the total to elute in an integrated elution curve as determined by a continuous temperature rising elution fractionation method (TREF) and a temperature T90 (° C.) allowing 90 wt % of the total to elute, and a weight average elution temperature Tw (° C.) satisfy the following relationship:

$$28 - 0.3 \times Tw \leq T90 - T10 \leq 41 - 0.3 \times Tw$$

As a twentieth invention, the present invention provides the ternary copolymer above, wherein the carbon number of the α-olefin is any of 4 to 8.

Advantage of the Invention

Copolymerization of an α-olefin and a ((meth)acrylic acid)-based olefin is performed in the presence of a polymerization catalyst according to the present invention, whereby an industrially useful α-olefin.((meth)acrylic acid)-based olefin copolymer having both a high molecular weight and a high comonomer content can be produced. Incidentally, this remarkable effect is verified by the data in the later-described Examples of the present invention and the comparison of Examples with Comparative Examples.

A catalyst component is supported on a fine particle support, whereby the properties of the produced polymer can be improved. In turn, particularly, the adaptability to a polymer production process requiring polymer particulation, such as slurry polymerization or vapor phase polymerization, can be improved.

This olefin copolymer is excellent in mechanical and thermal properties and applicable as a useful formed body. More specifically, the copolymer of the present invention can be applied to various uses such as film, sheet, adhesive resin, binder and compatibilizer, by utilizing its good properties in terms of, for example, coatability, printability, antistatic property, inorganic filler dispersibility, adhesion to other resins, and compatibilizing ability for other resins.

MODE FOR CARRYING OUT THE INVENTION

The present invention relates to novel triarylphosphine and triarylarsine compounds having a specific structure, a catalyst where such a novel compound is coordinated to a specific metal element, an α-olefin.((meth)acrylic acid)-based olefin copolymer using them, and a production process for two different kinds of α-olefin.((meth)acrylic acid)-based olefin copolymers.

Those novel compounds, the polymerization catalyst, the constituent components (monomer components) of the polymer, the production (polymerization) process, and the like are described in detail below.

1. Triarylphosphine and Triarylarsine Compounds

In the polymerization catalyst of the present invention, a novel triarylphosphine or triarylarsine compound working out to a ligand to a specific metal element is represented by the following formula (1):

[Chem. 5]

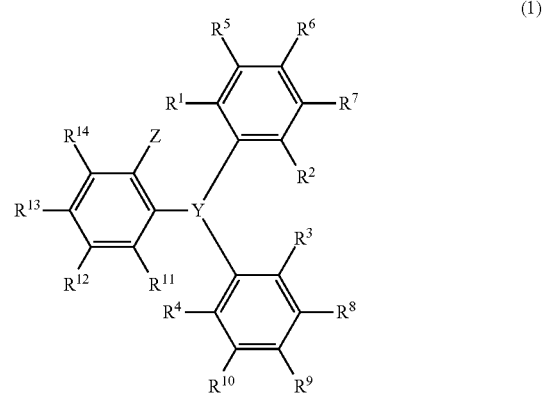

(wherein Y is phosphorus or arsenic, Z is —$SO_3H$ or $CO_2H$, each of $R^1$ to $R^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, at least one of $R^1$ to $R^4$ is a substituent where the carbon directly bonded to the aromatic ring is single-bonded to two or more elements selected from the group consisting of C, O and N, and each of $R^5$ to $R^{14}$ independently represents a hydrogen atom, a halogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, an aryloxy group having a carbon number of 6 to 30, or a silyl group substituted with a hydrocarbon group having a carbon number of 1 to 30).

Y is phosphorus or arsenic, preferably phosphorus. Z is —SO$_3$H or CO$_2$H, preferably —SO$_3$H.

Each of $R^1$ to $R^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, and at least one of $R^1$ to $R^4$ is a substituent where the carbon directly bonded to the aromatic ring is single-bonded to two or more elements selected from the group consisting of C, O and N. $R^1$ to $R^4$ are in the ortho-position with respect to the central Group 15 element (phosphorus or arsenic), that is, the triarylphosphine compound of the present invention has at least one sterically bulky substituent in the molecule (in the ortho-position), which is one of the characteristic features. Accordingly, at least one of $R^1$ and $R^2$ and at least one of $R^3$ and $R^4$ are preferably a substituent where the carbon directly bonded to the aromatic ring is single-bonded to two or more elements selected from the group consisting of C, O and N.

The substituent where the carbon directly bonded to the aromatic ring is single-bonded to two or more elements selected from the group consisting of C, O and N includes a secondary or tertiary alkyl group composed of two or more carbons C, an alkoxyalkyl group or cyclic ethers composed of one carbon C and one oxygen O, pyrrolidines or pyrroles composed of one carbon C and one nitrogen N, acetals composed of two oxygens O, morpholines or oxazoles composed of one oxygen O and one nitrogen N, and imidazolidines or imidazoles composed of two nitrogens N. The substituents containing two or more C, O or N may combine to form a ring. Among these, a secondary or tertiary alkyl group, an alkoxyalkyl group and cyclic ethers are preferred, and the later-described secondary or tertiary alkyl group and a tetrahydrofuryl group are more preferred.

The secondary or tertiary alkyl group means a group where the element directly bonded to the phenyl group is carbon and the site thereof is a secondary or tertiary alkyl group. Each of $R^1$ to $R^4$ which are a secondary or tertiary alkyl group is independently a hydrocarbon group having a carbon number of 3 to 30, which may contain a heteroatom.

Each of $R^1$ to $R^4$ when these are a secondary or tertiary alkyl group is independently a hydrocarbon group having a carbon number of 3 to 30, preferably a hydrocarbon group having a carbon number of 3 to 12, which is a secondary alkyl group, and more preferably a hydrocarbon group having a carbon number of 3 to 6. Specific preferred examples thereof include tricyclohexylmethyl group, 1,1-dimethyl-2-phenylethyl group, isopropyl group, 1,1-dimethylpropyl group, 1,1,2-trimethylpropyl group, 1,1-diethylpropyl group, 1-phenyl-2-propyl group, tertiary butyl group, isobutyl group, 1,1-dimethylbutyl group, 2-isopentyl group, 3-isopentyl group, 2-isohexyl group, 3-isohexyl group, 2-ethylhexyl group, 2-isoheptyl group, 3-isoheptyl group, 4-isoheptyl group, 2-propylheptyl group, 2-isooctyl group, 3-isononyl group, 1-adamantyl group, cyclopropyl group, cyclobutyl group, cyclopentyl group, methylcyclopentyl group, cyclohexyl group, methylcyclohexyl group, cycloheptyl group, cyclooctyl group, cyclododecyl group, exo-norbornyl group, endo-norbornyl group, 2-bicyclo[2.2.2]octyl group, 2-adamantyl group, nopinyl group, menthyl group, neomenthyl group and neopentyl group. Among these, isopropyl group, isobutyl group and cyclohexyl group are more preferred.

Each of $R^1$ to $R^4$ which are a secondary or tertiary alkyl group may contain a heteroatom in its partial structure. Introduction of an electron-donating group ascribable to the heteroatom can increase the electron density of the central metal spatially adjacent thereto and is effective for enhancing the catalytic activity. The heteroatom indicates, in a broad sense, a nonmetallic atom except for carbon atom, hydrogen atom and atoms of Groups 17 and 18 but is preferably a second- or third-row nonmetallic atom, more preferably an oxygen atom or a nitrogen atom, still more preferably an oxygen atom.

Each of these heteroatom-containing secondary or tertiary alkyl groups is independently an oxygen atom-containing secondary alkyl group having a carbon number of 4 to 30, preferably an oxygen atom-containing secondary alkyl group having a carbon number of 4 to 15, more preferably an oxygen atom-containing secondary alkyl group having a carbon number of 4 to 7, still more preferably an oxygen atom-containing secondary alkyl group having a carbon number of 4 to 7.

Specific preferred examples thereof include 1-(methoxymethyl)ethyl group, 1-(ethoxymethyl)ethyl group, 1-(phenoxymethyl)ethyl group, 1-(methoxyethyl)ethyl group, 1-(ethoxyethyl)ethyl group, 1-(dimethylaminomethyl)ethyl group, 1-(diethylaminomethyl)ethyl group, di(methoxymethyl)methyl group, di(ethoxymethyl)methyl group and di(phenoxymethyl)methyl group.

Each of $R^1$ to $R^4$ when these are not a secondary or tertiary alkyl group is independently a hydrogen atom, a hydrocarbon group having a carbon number of 1 to 30, a halogen atom-substituted hydroxyl group having a carbon number of 1 to 30, a heteroatom-containing hydrocarbon group having a carbon number of 1 to 30, an alkoxy group having a carbon number of 1 to 30, or an aryloxy group having a carbon number of 6 to 30.

The hydrocarbon group having a carbon number of 1 to 30 is preferably an alkyl group having a carbon number of 1 to 6, and specific preferred examples thereof include methyl group, ethyl group, normal-propyl group, n-butyl group and normal-hexyl group, with methyl group being more preferred.

The halogen atom-substituted hydrocarbon group having a carbon number of 1 to 30 is preferably an alkyl group having a carbon number of 1 to 6 and being substituted with one halogen atom. The halogen atom substituted is preferably a fluorine atom, and specific preferred examples thereof include fluoromethyl group, 1-fluoroethyl group, 2-fluoroethyl group, 3-fluoropropyl group, 4-fluorobutyl group and 6-fluorohexyl group.

The heteroatom-containing hydrocarbon group having a carbon number of 1 to 30 is preferably an oxygen atom-containing hydrocarbon group having a carbon number of 1 to 4, and specific preferred examples thereof include methoxymethyl group and ethoxymethyl group.

The alkoxy group having a carbon number of 1 to 30 is preferably an alkoxy group having a carbon number of 1 to 6, and specific preferred examples thereof include methoxy group and ethoxy group.

The aryloxy group having a carbon number of 6 to 30 is preferably an aryloxy group having a carbon number of 6 to 12, and specific preferred examples thereof include phenoxy group and 2-methylphenoxy group.

Among these specific examples of the substituent group when $R^1$ to $R^4$ are not a secondary or tertiary alkyl group, a hydrogen atom and an alkyl group having a carbon number of 1 to 6 are preferred, and a hydrogen atom and a methyl group are more preferred.

Each of $R^5$ to $R^{14}$ is independently a hydrogen atom, a halogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, an aryloxy group having a carbon number of 6 to 30, or a silyl group substituted with a hydrocarbon group having a carbon number of 1 to 30.

These substituents are a substituent at a site kept relatively distant from the central metal during complex formation and therefore, may be sufficient if it is a substituent not adversely affecting the formation of the phosphorus-sulfonic acid ligand complex. The electronic effect of these substituents is considered to affect the catalytic performance compared with their steric effect, and an electron-donating substituent is preferred. The substituents above may be the same or different.

Examples of the halogen atom include fluorine, chlorine and bromine.

Examples of the hydrocarbon group having a carbon number of 1 to 30 include an alkyl group, a cycloalkyl group, an alkenyl group and an aryl group.

Examples of the alkyl group and cycloalkyl group include methyl group, ethyl group, 1-propyl group, 1-butyl group, 1-pentyl group, 1-hexyl group, 1-heptyl group, 1-octyl group, 1-nonyl group, 1-decyl group, tert-butyl group, tricyclohexylmethyl group, 1,1-dimethyl-2-phenylethyl group, isopropyl group, 1-dimethylpropyl group, 1,1,2-trimethylpropyl group, 1,1-diethylpropyl group, 1-phenyl-2-propyl group, isobutyl group, 1,1-dimethylbutyl group, 2-pentyl group, 3-pentyl group, 2-hexyl group, 3-hexyl group, 2-ethylhexyl group, 2-heptyl group, 3-heptyl group, 4-heptyl group, 2-propylheptyl group, 2-octyl group, 3-nonyl group, cyclopropyl group, cyclobutyl group, cyclopentyl group, cyclopropyl group, methylcyclopentyl group, cyclohexyl group, methylcyclohexyl group, cycloheptyl group, cyclooctyl group, cyclododecyl group, 1-adamantyl group, 2-adamantyl group, exo-norbornyl group, endo-norbornyl group, 2-bicyclo[2,2,2]octyl group, nopinyl group, decahydronaphthyl group, menthyl group, neomenthyl group, neopentyl group and 5-decyl group. Among these substituents, isopropyl group, isobutyl group and cyclohexyl group are preferred.

The alkenyl group includes vinyl group, allyl group, butenyl group, cinnamyl group and styryl group.

The aryl group includes phenyl group, naphthyl group, anthracenyl group and fluorenyl group. Examples of the substituent which can be present on the aromatic ring of such an aryl group include an alkyl group, an aryl group, a fused aryl group, a phenylcyclohexyl group, a phenylbutenyl group, a tolyl group, a xylyl group, a p-ethylphenyl group and a pentafluorophenyl group. Among these substituents, phenyl group and pentafluorophenyl group are preferred.

The halogen atom-substituted hydrocarbon group having a carbon number of 1 to 30 is a substituent where the above-described hydrocarbon group having a carbon number of 1 to 30 is substituted with a halogen atom such as fluorine, chlorine and bromine.

The heteroatom which may be contained in the heteroatom-containing hydrocarbon group having a carbon number of 1 to 30 is preferably an oxygen atom or a nitrogen atom. Specific examples of the heteroatom-containing hydrocarbon group having a carbon number of 1 to 30 include $OR^{15}$, $CO_2R^{15}$, $CO_2M'$, $C(O)N(R^{15})_2$, $C(O)R^{15}$, $SO_2R^{15}$, $SOR^{15}$, $OSO_2R^{15}$, $P(O)(OR^{15})_{2-y}(R^{16})_y$, CN, $NHR^{15}$, $N(R^{15})_2$, $NO_2$, $SO_3M'$, $PO_3M'_2$, $P(O)(OR^{15})_2M'$, and a hydrocarbon group having a substituent containing a heteroatom, such as epoxy group. Here, M' represents an alkali metal, an alkaline earth metal, an ammonium, a quaternary ammonium or a phosphonium, x represents an integer of 0 to 3, y represents an integer of 0 to 2, $R^{15}$ represents hydrogen or a hydrocarbon group having a carbon number of 1 to 20, and $R^{16}$ represents a hydrocarbon group having a carbon number of 1 to 20. Among these heteroatom-containing substituents, $OR^{15}$ and $N(R^{15})_2$ are preferred, and $OR^{15}$ is more preferred.

The alkoxy group having a carbon number of 1 to 30 is preferably an alkoxy group having a carbon number of 1 to 6, and specific preferred examples include methoxy group and ethoxy group.

The aryloxy group having a carbon number of 6 to 30 is preferably an aryloxy group having a carbon number of 6 to 12, and specific preferred examples thereof include phenoxy group and 2-methylphenoxy group.

The silyl group substituted with a hydrocarbon group having a carbon number of 1 to 30 is preferably a silyl group having a carbon number of 3 to 18, and specific preferred examples thereof include trimethylsilyl group, dimethylphenylsilyl group, diphenylmethylphenylsilyl group and triphenylsilyl group.

The ligand of the present invention is estimated to be a chelating or potentially chelating ligand. For example, it has been reported that a ligand having an —$SO_3H$ group becomes a chelated metal complex by complexing with palladium (Non-Patent Document 3) and a ligand having a —$CO_2H$ group becomes a chelated metal complex by complexing with nickel (Non-Patent Document 4).

2. Synthesis of Triarylphosphine or Triarylarsine Compound

Synthesis of the triarylphosphine compound as the first invention is performed through the following route. That is, some synthesis routes are known for the compound, and specific examples thereof include a route where a lithio form of an aryl group (aryl lithium salt) to be introduced is reacted with the raw material phosphorus trichloride in an appropriate molar ratio. After the reaction, extraction under acidic conditions and washing follow, whereby the target product can be obtained. Synthesis of the triarylarsine compound is performed in the same manner.

3. Synthesis of Polymerization Catalyst

The polymerization catalyst of the present invention is an α-olefin polymerization catalyst obtained by reacting the novel triarylphosphine or triarylarsine compound represented by formula (1) and a Group 8-10 transition metal compound.

Synthesis of the catalyst composition is generally performed by bringing a Group 8-10 transition metal compound into contact with the ligand in a solution or a slurry. The transition metal compound is preferably a Group 10 transition metal compound, and the synthesis is performed using, for example, bis(dibenzylideneacetone)palladium, tetrakis(triphenylphosphine)palladium, palladium sulfate, palladium acetate, bis(allylpalladium chloride), palladium chloride, palladium bromide, (cyclooctanediene)palladium (methyl)chloride, dimethyl (tetramethylethylenediamine)palladium, bis(cyclooctadiene)nickel, nickel chloride, nickel bromide, (tetramethylethylenediamine)nickel (methyl)chloride, dimethyl (tetramethylethylenediamine)nickel or (cyclooctadiene)nickel (methyl)chloride.

The complexing reaction may be performed in a reaction vessel for use in the copolymerization with an α-olefin or may be performed in a separate vessel different from the reaction vessel. After the complex formation, the metal complex may be isolated by extraction and used for a catalyst or may be used for a catalyst without isolation. It is also possible to perform the reaction in the presence of the later-described porous support. Furthermore, as for the catalyst composition of the present invention, one kind of a catalyst composition may be used alone, or a plurality of kinds of catalyst compositions may be used in combination. In particular, the combination use of a plurality of kinds of catalyst compositions is useful for the purpose of broadening the molecular weight distribution or the comonomer content distribution.

The metal complex obtained by reacting a triarylphosphine or triarylarsine compound represented by formula (1) and a Group 8-10 transition metal compound may be a metal complex represented by the following formula (2):

[Chem. 6]

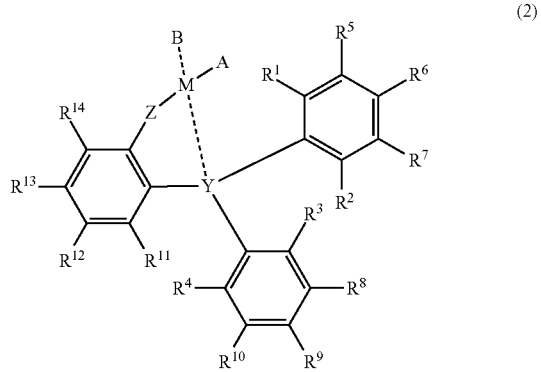

(2)

(wherein Y is phosphorus or arsenic, Z is —SO$_3$— or CO$_2$—, each of R$^1$ to R$^4$ independently represents a hydrogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, or an aryloxy group having a carbon number of 6 to 30, at least one of R$^1$ to R$^4$ is a substituent where the carbon directly bonded to the aromatic ring is single-bonded to two or more elements selected from the group consisting of C, O and N, each of R$^5$ to R$^{14}$ independently represents a hydrogen atom, a halogen atom, a hydrocarbon group having a carbon number of 1 to 30, a halogen atom-substituted hydrocarbon group having a carbon number of 1 to 30, a heteroatom-containing hydrocarbon group having a carbon number of 1 to 30, an alkoxy group having a carbon number of 1 to 30, an aryloxy group having a carbon number of 6 to 30, or a silyl group substituted with a hydrocarbon group having a carbon number of 1 to 30, M represents a metal atom selected from the group consisting of transition metals of Groups 8 to 10, A represents a hydrogen atom, a halogen atom, an alkyl group having a carbon number of 1 to 30, which may have a heteroatom, or an aryl group having a carbon number of 6 to 30, which may have a heteroatom, B represents an arbitrary ligand coordinated to M, and A and B may combine with each other to form a ring).

Here, Y, Z and R$^1$ to R$^{14}$ are the same as the substituents in the triarylphosphine or triarylarsine compound represented by formula (1).

M represents a Group 8-10 transition metal and is preferably Fe, Co, Ni, Pd, Pt or lanthanide, more preferably Ni or Pd.

A represents a hydrogen atom, a halogen atom, an alkyl group having a carbon number of 1 to 30, which may have a heteroatom, or an aryl group having a carbon number of 6 to 30, which may have a heteroatom. The heteroatom is preferably an oxygen atom, a nitrogen atom or a silicon atom, more preferably an oxygen atom.

The alkyl group is preferably an alkyl group having a carbon number of 1 to 6, and examples thereof include a methyl group, an ethyl group, a trifluoromethyl group, an acyl group and an acetoxy group. The aryl group is preferably an aryl group having a carbon number of 6 to 13, and examples thereof include a phenyl group, a tolyl group, a xylyl group, a phenacyl group and a pentafluorophenyl group. Among these substituents, a hydrogen atom, a methyl group and a phenyl group are preferred.

B is an arbitrary ligand coordinated to M. This ligand is a hydrocarbon compound having a carbon number of 1 to 20 and containing oxygen, nitrogen, phosphorus or sulfur as an atom capable of coordination bonding. Specific examples of the ligand include phosphines, pyridine derivatives, piperidine derivatives, alkyl ether derivatives, aryl ether derivatives, alkylaryl ether derivatives, ketones, cyclic ethers, alkylnitrile derivatives, arylnitrile derivatives, alcohols, amides, aliphatic esters, aromatic esters and amines. Preferred ligands are ketones, cyclic ethers, phosphines and pyridine derivatives, and more preferred ligands are acetone, tetrahydrofuran, pyridine, lutidine and triphenylphosphine.

4. Fine Particle Support

As for the fine particle support used in the present invention, an arbitrary fine particle support can be used as long as the purport of the present invention is not impaired.

In general, an inorganic oxide or a polymer support can be suitably used. Specific examples thereof include SiO$_2$, Al$_2$O$_3$, MgO, ZrO$_2$, TiO$_2$, B$_2$O$_3$, CaO, ZnO, BaO, ThO$_2$ and a mixture thereof. A mixed oxide such as SiO$_2$—Al$_2$O$_3$, SiO$_2$—V$_2$O$_5$, SiO$_2$—TiO$_2$, SiO$_2$—MgO and SiO$_2$—Cr$_2$O$_3$ can be also used, and an inorganic silicate, a polyethylene support, a polypropylene support, a polystyrene support, a polyacrylic acid support, a polymethacrylic acid support, a polyacrylic ester support, a polyester support, a polyamide support, a polyimide support and the like can be used. Among these supports, a support composed of an inorganic oxide is preferred, an ion-exchanging layered silicate is more preferred. Still more preferably, the smectite group is used.

Examples of the ion-exchanging layered silicate which can be used include clay, clay mineral, zeolite and diatomaceous earth. For these materials, a synthesized product may be used or a naturally occurring mineral may be used.

Specific examples of the clay and clay mineral include the allophane family such as allophane; the kaolin family such as dickite, nacrite, kaolinite and anauxite; the halloysite family such as metahalloysite and halloysite; the serpentine family such as chrysotile, lizardite and antigorite; the smectite family such as montmorillonite, sauconite, beidellite, nontronite, saponite and hectorite; the vermiculite family such as vermiculite; a mica mineral such as illite, sericite and glauconite; attapulgite; sepiolite; palygorskite; bentonite; kibushi clay; gairome clay; hisingerite; pyrophyllite; and a group of chlorites. These may form a mixed layer.

Examples of the artificially synthesized product include a synthetic mica, a synthetic hectorite, a synthetic saponite and a synthetic taeniolite.

Among these specific examples, preferred are the kaolin family such as dickite, nacrite, kaolinite and anauxite, the halloysite family such as metahalloysite and halloysite, the serpentinite family such as chrysotile, rizaldite and antigorite, the smectite family such as montmorillonite, sauconite, beidellite, nontronite, saponite and hectorite, a vermiculite mineral such as vermiculite, a mica mineral such as illite, sericite and glauconite, a synthetic mica, a synthetic hectorite, a synthetic saponite and a synthetic taeniolite, and more preferred are the smectite family such as montmorillonite, sauconite, beidellite, nontronite, saponite and hectorite, a vermiculite mineral such as vermiculite, a synthetic mica, a synthetic hectorite, a synthetic saponite and a synthetic taeniolite.

Such a fine particle support may be used directly or may be subjected to an acid treatment with hydrochloric acid, nitric acid, sulfuric acid or the like and/or a treatment with salts such as LiCl, NaCl, KCl, $CaCl_2$, $MgCl_2$, $Li_2SO_4$, $MgSO_4$, $ZnSO_4$, $Ti(SO_4)_2$, $Zr(SO_4)_2$ and $Al_2(SO_4)_3$. In the treatment, corresponding acid and base may be mixed to produce a salt in the reaction system, thereby effecting the treatment, or a shape control such as pulverization or granulation or a drying treatment may be performed.

The fine particle support is not particularly limited in its particle diameter and the like, and an arbitrary fine particle may be used, but the particle diameter in terms of the average particle diameter is preferably from 5 to 200 μm, more preferably from 10 to 100 μm.

The fine particle support may be treated with an organic aluminum compound before use. The organic aluminum compound used here has a substituent selected from an alkyl group having a carbon number of 1 to 20, a halogen, hydrogen, an alkoxy group and an amino group. Among these substituents, an alkyl group having a carbon number of 1 to 20, hydrogen and an alkoxy group having a carbon number of 1 to 20 are preferred, and an alkyl group having a carbon number of 1 to 20 is more preferred. When a plurality of substituents are present, they may be the same or different. As for the organic aluminum compound, one kind of a compound may be used alone, or a plurality of kinds of compounds may be used in combination.

Specific examples of the organic aluminum compound include trimethylaluminum, triethylaluminum, tri-normal-propylaluminum, tri-n-butylaluminum, triisobutylaluminum, tri-normal-hexylaluminum, tri-normal-octylaluminum, tri-normal-decylaluminum, diethylaluminum chloride, diethylaluminum sesquichloride, diethylaluminum hydride, diethylaluminum ethoxide, diethylaluminum dimethylamide, diisobutylaluminum hydride and diisobutylaluminum chloride. Among these, preferred are a trialkylaluminum and an alkylaluminum hydride, and more preferred is a trialkylaluminum having a carbon number of 1 to 8.

5. Use Mode of Polymerization Catalyst
(1) Contact of Catalyst Components

The triarylphosphine or triarylarsine compound, the Group 8-10 transition metal compound and the fine particle support can be contacted in an arbitrary order. In contacting the components, each component may be contacted in the form of a solid or may be formed into a solvent slurry or a uniform solution and then contacted. Examples of the order of contacting respective components include:

contact order 1: The triarylphosphine or triarylarsine compound and the Group 8-10 transition metal compound are contacted and then contacted with the fine particle support;

contact order 2: The triarylphosphine or triarylarsine compound and the fine particle support are contacted and then contacted with the Group 8-10 transition metal compound; and contact order 3: The Group 8-10 transition metal compound and the fine particle support are contacted and then contacted with the triarylphosphine or triarylarsine compound.

Among these contacting methods, the contact order 1 is preferred. Also, after contacting the fine particle support with other catalyst components, the support may be washed with a solvent having no reactivity with the catalyst components. The solvent is preferably a hydrocarbon solvent or a halogenated hydrocarbon.

The triarylphosphine or triarylarsine compound is used in an amount of usually from 0.001 to 10 mmol, preferably from 0.001 to 1 mmol, per 1 g of the fine particle support.

As for the temperature at which respective components are contacted, the contact may be performed at an arbitrary temperature as long as it is not more than the boiling point of the solvent, but the temperature is preferably from room temperature to the boiling point of the solvent.

The contacted catalyst components may be used directly for polymerization evaluation or may be dried to a solid state and stored. Furthermore, preliminary polymerization described below may be also performed.
(2) Preliminary Polymerization The contacted catalyst components may be subjected to preliminary polymerization in the presence of an olefin by contacting the components inside or outside the polymerization tank. The olefin indicates a hydrocarbon containing at least one carbon-carbon double bond, and examples thereof include ethylene, propylene, 1-butene, 1-hexene, 3-methylbutene-1, styrene and divinylbenzene. However, the kind of the olefin is not particularly limited, and a mixture of such a hydrocarbon with another olefin may be also used. An olefin having a carbon number of 2 or 3 is preferred. The method for supplying the olefin may be an arbitrary method, for example, may be a method of supplying the olefin to the reaction tank at a constant rate or in a manner to keep the constant pressure state, a method of combining these methods, or a method of stepwise changing the rate or pressure.

6. Monomers Used

The monomers used in the production of the copolymer include an α-olefin, a ((meth)acrylic acid)-based olefin and other olefins, which are described below.

(a) α-Olefin

One of the monomers for use in the present invention is an α-olefin represented by the formula: $CH_2=CHR^{17}$ (hereinafter sometimes referred to as a "component (a)"). Here, $R^{17}$ is hydrogen or an alkyl group having a carbon number of 1 to 20.

The component (a) is preferably an α-olefin with $R^{17}$ having a carbon number of 1 to 10. The component (a) is more preferably ethylene, propylene, 1-butene, 1-pentene, 1-hexene, 1-octene, 1-decene, 3-methyl-1-butene or 4-methyl-1-pentene, still more preferably propylene, 1-butene, 1-pentene, 1-hexane or 1-octane, yet still more preferably 1-hexene. Incidentally, one component (a) may be used alone, or a plurality of components (a) may be used in combination.

(b) ((Meth)Acrylic Acid)-Based Olefin

Another of the monomers for use in the present invention is a (meth)acrylic acid or a (meth)acrylic ester represented by the formula: $CH_2=C(R^{18})CO_2(R^{19})$ (hereinafter, these are sometimes collectively referred to as a "component (b)" or a "(meth)acrylic acid (or ester)"). Here, $R^{18}$ is hydrogen or a hydrocarbon group having a carbon number of 1 to 10 and my have a branch, a ring and/or an unsaturated bond, $R^{19}$ is hydrogen or an alkyl group having a carbon number of 1 to 30, and $R^{19}$ may contain a heteroatom in an arbitrary position.

The component (b) is preferably a (meth)acrylic ester with $R^{18}$ having a carbon number of 1 to 5 or a (meth)acrylic acid. The component (b) is more preferably a methacrylic ester with $R^{18}$ being a methyl group, an acrylic ester with $R^{18}$ being hydrogen, or a (meth)acrylic acid. The component (b) is still more preferably, for example, methyl acrylate, ethyl acrylate, n-propyl acrylate, isopropyl acrylate, n-butyl acrylate, isobutyl acrylate, tert-butyl acrylate, pentyl acrylate, hexyl acrylate, cyclohexyl acrylate, octyl acrylate, 2-ethylhexyl acrylate, nonyl acrylate, decyl acrylate, dodecyl acrylate, phenyl acrylate, toluoyl acrylate, benzyl acrylate, hydroxyethyl acrylate, glycidyl acrylate, or acrylic acid. One component (b) may be used alone, or a plurality of components (b) may be used in combination.

(c) Other Olefins

Still another of the monomers for use in the present invention is other olefins (hereinafter sometimes referred to as a "component (c)").

Preferred examples of the component (c) include a cyclic olefin monomer such as cyclopentene, cyclohexene, norbornene and ethylidenenorbornene, and a styrene-based monomer such as p-methylstyrene. The skeletal structure of such a monomer may contain a hydroxyl group, an alkoxide group, a carboxylic acid group, an ester group or an aldehyde group.

The norbornene-based olefin can be produced by a Diels-Alder reaction ([4+2]cycloaddition) using cyclopentadiene. The dienophile used is, for example, diethyl azodicarboxylate, aldehyde, maleic anhydride, dihydrofuran, vinylpyridine, an alkyl acrylate or the above-described substituted olefin (see, T. L. Gilchrist, *Heterocyclic Chemistry*, Chap. 4.3.3, 1985). These monomers can be represented by formulae (3a) to (3f), wherein $R^{20}$ is a hydrocarbon group having a carbon number of 1 to 30 and may contain a branch, a ring or an unsaturated bond.

The monomer specified in the component (a) may be also a hydroxyl group-containing monomer such as (3-buten)-1-ol, an ether group-containing monomer such as methyl vinyl ether, a carboxylic acid group-containing monomer such as acrylic acid, an ester group-containing monomer such as methyl acrylate, or a monomer containing an aldehyde group or the like, such as acrolein. In addition, a diene derivative, a maleic anhydride, a vinyl acetate or the like is also usable.

[Chem. 7]

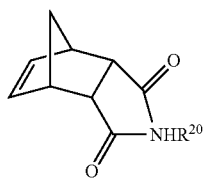
(3a)

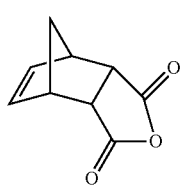
(3b)

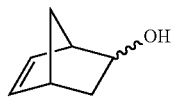
(3c)

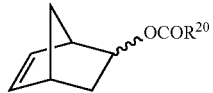
(3d)

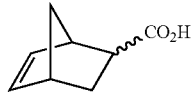
(3e)

(3f)

7. Copolymerization Reaction

In the present invention, the copolymerization reaction is preformed in the presence or absence of a hydrocarbon solvent such as propane, n-butane, isobutane, n-hexane, n-heptane, toluene, xylene, cyclohexane, methylcyclohexane, a liquid such as liquefied α-olefin, or a polar solvent such as diethyl ether, ethylene glycol dimethyl ether, tetrahydrofuran, dioxane, ethyl acetate, methyl benzoate, acetone, methyl ethyl ketone, formamide, acetonitrile, methanol, isopropyl alcohol and ethylene glycol. Also, a mixture of liquid compounds described here may be used as the solvent. In the case of obtaining high polymerization activity or a high molecular weight, a hydrocarbon solvent described above is preferred.

In performing the copolymerization of the present invention, the copolymerization may be performed in the presence or absence of known additives. The additive is preferably a radical polymerization inhibitor or an additive having an action of stabilizing the copolymer produced. Preferred examples of the additive include a quinone derivative and a hindered phenol derivative. Specific examples of the additive which can be used include monomethyl ether hydroquinone, 2,6-di-tert-butyl 4-methylphenol (BHT), a reaction product of trimethylaluminum and BHT, and a reaction product of tetravalent titanium, alkoxide and BHT. Also, an inorganic or organic filler may be used as the additive, and the polymerization may be performed in the presence of such a filler.

In the present invention, the polymerization form is not particularly limited and, for example, slurry polymerization where at least a part of the produced polymer becomes a slurry in a medium, bulk polymerization where the liquefied monomer itself works as a medium, vapor phase polymerization where the polymerization is performed in vaporized monomers, and high-pressure ionic polymerization where at least a part of the produced polymer dissolves in monomers liquefied at a high temperature under a high pressure, is preferably employed.

The polymerization form may be any of batch polymerization, semi-batch polymerization and continuous polymerization or may be living polymerization, or the polymerization may be also performed while allowing chain transfer to occur in parallel. Furthermore, a chain shuttling reaction or coordinative chain transfer polymerization (CCTP) may be performed by using a so-called chain shuttling agent (CSA) in combination.

The unreacted monomer or medium is separated from the produced copolymer and may be recycled. At the recycle, such a monomer or medium may be purified and then reused or may be reused without purification. For the separation of the unreacted monomer and the medium from the produced copolymer, a conventionally known method may be used. Examples of the method which can be used include filtration, centrifugal separation, solvent extraction, and reprecipitation using a poor solvent.

The copolymerization temperature, copolymerization pressure and copolymerization time are not particularly limited but usually, can be optimally set in the following ranges by taking into consideration the productivity and the processing ability.

That is, these can be selected from the ranges where the copolymerization temperature is usually from −20° C. to 300° C., preferably from 0 to 250° C., more preferably from 50 to 100° C., the copolymerization pressure is preferably from 0.1 to 200 MPa, preferably from 0.3 to 100 MPa, more preferably from 0.3 to 5 MPa, and the copolymerization time is from 0.1 minutes to 6 hours, preferably from 0.5 minutes to 5 hours, more preferably from 10 minutes to 4 hours.

In the present invention, the copolymerization is generally performed in an inert gas atmosphere. for example, a nitrogen, argon or carbon dioxide atmosphere can be used, and a nitrogen atmosphere is preferably used. A small amount of oxygen or air may be mixed.

The supply of the catalyst and monomers to the copolymerization reactor is also not particularly limited, and various supply methods may be employed according to the purpose. For example, in the case of batch polymerization, a technique of previously supplying predetermined amounts of the monomers to the copolymerization reaction and supplying the catalyst thereto may be employed. In this case, an additional monomer or an additional catalyst may be supplied to the copolymerization reactor. In the case of continuous polymerization, a technique of continuously or intermittently supplying predetermined amounts of the monomers and the catalyst to the copolymerization reactor to continuously perform the copolymerization reaction may be employed.

As for the control of the composition of the copolymer, a method of supplying a plurality of monomers to the reactor and changing the supply ratio, thereby controlling the composition, can be generally used. In addition, a method of controlling the copolymerization composition by utilizing the difference in the monomer reactivity ratio due to difference in the catalyst structure, or a method of controlling the copolymerization composition by utilizing the polymerization temperature dependency of the monomer reactivity ratio, may be used.

For the control of the molecular weight of the copolymer, a conventionally known method can be used. That is, examples of the method include a method of controlling the molecular weight by controlling the polymerization temperature, a method of controlling the molecular weight by controlling the monomer concentration, a method of controlling the molecular weight by using a chain transfer agent, and a method of controlling the molecular weight by controlling the ligand structure in the transition metal complex.

In the case of using a chain transfer agent, a conventionally known chain transfer agent can be used. Examples of the chain transfer agent which can be used include hydrogen and a metal alkyl. In the case where the component (b) or (c) itself works as a kind of chain transfer agent, the molecular weight can be also adjusted by controlling the concentration of the component (b) or (c) or the ratio to the component (a). In the case of adjusting the molecular weight by controlling the ligand structure in the transition metal complex, there may be utilized a tendency that the molecular weight is generally increased by disposing a bulky substituent around the metal M, by disposing an electron-donating group such as aryl group and heteroatom-containing substituent in such a manner as to enable interaction with the metal M, or by introducing a heteroatom into $R^{18}$ to $R^{20}$.

8. Ternary Copolymer of Ethylene-α Olefin-(Meth)Acrylic Acid (or Ester)

As described above, the α olefin polymerization catalyst of the present invention can polymerize a polar group-containing monomer such as (meth)acrylic acid (or ester), and in particular, a ternary copolymer of ethylene-α olefin-(meth) acrylic acid (or ester) produced using the catalyst of the present invention has the following novel properties.

That is, the ternary copolymer of the present invention is a ternary copolymer of an ethylene, an α-olefin having a carbon number of 3 to 10 and a (meth)acrylic acid or ester represented by $CH_2=C(R^{18})CO_2(R^{19})$ (wherein $R^{18}$ is hydrogen or an alkyl group having a carbon number of 1 to 10, and $R^{19}$ is hydrogen or an alkyl group having a carbon number of 1 to 30, which may contain a hydroxyl group, an alkoxy group or an epoxy group on an arbitrary position), the ternary copolymer satisfying the following requirements (a) and (b):

(a) the ratio Mw/Mn of the weight average molecular weight (Mw) to the number average molecular weight (Mn) satisfies the following relationship:

$$1.5 \leq Mw/Mn \leq 3$$

(b) the melting point Tm (° C.), the α-olefin content [C] (mol %) and the polar group-containing vinyl monomer content [X] (mol %) satisfy the following relationship:

$$60 \leq Tm \leq 135 - 6.4 \times ([C]+[X])$$

wherein Tm is the peak temperature of a melting curve obtained by the measurement using a differential scanning calorimeter (DSC) and when a plurality of melting peaks are detected, Tm is the temperature of the maximum peak out of detected peaks.

Mw/Mn of the copolymer of the present invention must be 3.0 or less, and Mw/Mn is preferably 2.7 or less, more preferably 2.4 or less. If Mw/Mn exceeds 3, the mechanical strength, particularly the impact strength, decreases.

Mw/Mn of the copolymer of the present invention is 1.5 or more. It is difficult to industrially produce a copolymer having Mw/Mn of less than 1.5.

In the ternary copolymer of the present invention, the melting point Tm (° C.), the α-olefin content [C] (mol %) and the polar group-containing vinyl monomer content [X] (mol %) must satisfy the relationship of $60 \leq Tm \leq 135-6.4 \times ([C]+[X])$. The melting point changes according to how the α-olefin and/or polar group-containing vinyl monomer copolymerized are arranged in the molecular chain. In the case where the α-olefin or the polar group-containing monomer is unevenly distributed to, for example, the terminal of the molecular chain, the crystallizable ethylene chain becomes long on average and this brings a high melting point even when ([C]+[X]) is the same. On the other hand, in the case where the α-olefin or the polar group-containing monomer is uniformly distributed inside the molecular chain, the melting point lowers. If the melting point is less than 60° C., the minimum heat resistance required of an ethylene-based copolymer cannot be retained, whereas if the melting point exceeds 135−6.4×([C]+ [X]), the crystal lamella becomes thick and the number of tie molecules connecting a lamella and a lamella is decreased, as a result, the mechanical properties such as impact strength are impaired.

Also, for attaining the objects of the present invention, the phase angle δ(G*=0.1 MPa) at G*=0.1 MPa as measured by a rotary rheometer is preferably 40° or more. The δ(G*=0.1 MPa) is sensitive to both the molecular weight distribution and the long-chain branch but as far as a copolymer with Mw/Mn≤3 is concerned, the phase angle is indicative of the amount of the long-chain branch, and as the amount of the long-chain branch is larger, the value of δ(G*=0.1 MPa) becomes smaller. If the value of δ(G*=0.1 MPa) is less than 40°, the amount of the long-chain branch is too large and therefore, the mechanical strength decreases. In the copolymer of the present invention, Mw/Mn is 1.5 or more and therefore, even when the copolymer has no long-chain branch, the value of δ(G*=0.1 MPa) does not exceed 75°.

Furthermore, for attaining the objects of the present invention, the difference T90−T10 (° C.) between the temperature T10 (° C.) allowing 10 wt % of the total to elute in an integrated elution curve as determined by the continuous temperature rising elution fractionation method (TREF) and the temperature T90 (° C.) allowing 90 wt % of the total to elute and the weight average elution temperature Tw (° C.) preferably satisfy the following relationship:

$$28-0.3\times Tw \leq T90-T10 \leq 41-0.3\times Tw$$

T90−T10 is a parameter indicating the width of the composition distribution and as this value is larger, the composition distribution is wider, that is, the difference in the α-olefin and/or polar group-containing vinyl monomer contents is larger among different molecular chains. If the relationship of T90−T10≤41−0.3×Tw is not satisfied, the composition distribution is wide and the low crystalline component giving rise to stickiness and die lip build up is increased, as a result, the physical properties or outer appearance of the formed body are impaired. On the other hand, it is difficult to produce a copolymer not satisfying 28−0.3×Tw≤90−T10.

The parameter T90−T10 indicating the width of the composition distribution is expressed as a function of the average elution temperature Tw because of the following reasons. The average elution temperature Tw represents an average ethylene chain length of the copolymer and as the Tw value is higher, the average chain length is longer. When the Tw value becomes low, that is, when the average ethylene chain length becomes short, this means that a larger amount of short-chain branches or the like which inhibit the crystallization are introduced into the molecular chain. Usually, in a random copolymer, short-chain branches are not introduced at regular intervals but the interval has a distribution and when many short-chain branches are introduced, the interval distribution is broadened. As a result, even in the case of a copolymer polymerized using the same catalyst, when T90−T10 is plotted with respect to Tw, a right-rising relationship is obtained. The same applies to a copolymer produced using the conventional metallocene-based catalyst. The coefficient 0.3 of Tw is an experimental value obtained from the gradient of the Tw vs. T90−T10 plot of an ethylene-hexene-1 copolymer polymerized using a metallocene catalyst having uniform active sites. Also, the intercept 28 in the expression of lower limit of the formula above is determined based on the average elution temperature of an ethylene homopolymer, that is, about 95° C., such that T90−T10 becomes about 0 when Tw=95° C. On the other hand, the intercept 41 in the expression of upper limit is determined based on the fact that all Examples of the present invention are covered.

MFR of the copolymer of the present invention is preferably from 0.01 to 100, more preferably from 0.02 to 30, still more preferably from 0.05 to 10. If MFR is less than 0.01, moldability is poor, whereas if it exceeds 100, the strength decreases.

The mechanical properties of an ethylene-based copolymer by the conventional metallocene system containing no polar group are substantially determined by the average molecular weight and the comonomer content, because both the composition distribution and the molecular weight distribution are narrow.

Meanwhile, (surprisingly), despite the same narrow composition distribution and narrow molecular weight distribution as those of an ethylene-based copolymer by the conventional metallocene system, mechanical properties of the copolymer of the present invention are not an extension of the ethylene-based copolymer by the conventional metallocene system. More specifically, the elastic modulus and yielding stress vary in correspondence to the monomer content and therefore, for example, even a copolymer having the same elastic modulus or yielding stress can be obtained as a copolymer excellent in the heat resistance.

The reason therefor is not clearly known but is presumed to be that both the polar group moiety and the α-olefin-derived short-chain branch moiety in the copolymer are kept away from the crystal portion of the polyethylene and unevenly distributed in a high concentration to the non-crystal portion and because of poor compatibility due to difference in the polarity, they cause an increase in the free volume of the non-crystal part.

As additional conditions for attaining the objects of the present invention, the total amount of branches except for branch structures derived from the side chain substituent represented by $R^{17}$ in the formula above of the α-olefin and the $COO(R^{19})$ group of the (meth)acrylic acid (or ester) is preferably 1/1,000 C or less.

Out of (meth)acrylic acid (or ester) monomer units forming the ternary copolymer of ethylene-α olefin-(meth)acrylic acid (or ester) of the present invention, the amount of (meth)acrylic acid (or ester) monomer units present in the terminal of the copolymer is preferably 20% or less, more preferably 5% or less, still more preferably 1% or less, based on the amount of all (meth)acrylic acid (or ester) monomer units contained in the copolymer, and it is preferred that a (meth)acrylic acid (or ester) monomer unit is substantially not present in the terminal. If the ratio of the unit present in the terminal exceeds 20%, the impact strength or elongation characteristic of the copolymer becomes insufficient.

9. Method for Controlling Ternary Copolymer of Ethylene-α Olefin-(Meth)Acrylic Acid (or Ester)

The ternary copolymer of the present invention must have a molecular weight distribution where Mw/Mn is 1.5 or more and Mw/Mn is 3.0 or less, and Mw/Mn is preferably 2.7 or less, more preferably 2.4 or less.

As regards the control method therefor, the ternary copolymer above can be produced by using the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound. This considered to be achieved because the catalyst above is less susceptible to deterioration of the active site even in the presence of a polar monomer and maintains homogeneous active species. Furthermore, by reducing the change in the temperature or the monomer or comonomer concentration during the polymerization, a copolymer with a narrow molecular weight distribution can be produced. Here, Mw/Mn can be made small to a certain extent by such a technique, but it is difficult to produce a copolymer having Mw/Mn of less than 1.5.

In the ternary copolymer of the present invention, the melting point Tm (° C.), the α-olefin content [C] (mol %) and the polar group-containing vinyl monomer content [X] (mol %) must satisfy the relationship of $60 \leq Tm \leq 135-6.4 \times ([C]+[X])$. For this purpose, copolymerization must be caused to proceed so that a composition the α-olefin and the polar group-containing vinyl monomer can be homogenized in the composition.

As regards the control method therefor, in the case of the comonomer content, the pressure and concentration ratio of the ethylene, α-olefin and polar group-containing vinyl monomer are controlled, whereby the melting point Tm (° C.) and the contents of the α-olefin and the polar group-containing vinyl monomer can be changed and the melting point can be controlled. Although it depends on the ethylene pressure, for example, when the ethylene pressure is 2 MPa, a copolymer having a desired comonomer content in the range of the α-olefin and the polar group-containing vinyl monomer being from 0.01 to 9.0 mol/L can be produced and the melting point can be controlled. Also, the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, is less susceptible to deterioration of the active site even in the presence of a polar monomer and maintains homogeneous active species. Furthermore, in addition to the copolymerizability of the polar monomer, the copolymerizability of 1-hexene which has been heretofore difficult to copolymerize is improved as compared with the conventionally known catalyst, Accordingly, for effecting the control above, it is important to select the catalyst of the present invention.

Also, in the ternary copolymer of the present invention, the phase angle $\delta(G^*=0.1 \text{ MPa})$ at $G^*=0.1$ MPa as measured by a rotary rheometer is preferably 40° or more. The $\delta(G^*=0.1 \text{ MPa})$ is indicative of the amount of the long-chain branch and when the amount of the long-chain branch is large, the value of $\delta(G^*=0.1 \text{ MPa})$ becomes small. If the value of $\delta(G^*=0.1 \text{ MPa})$ is less than 40°, the amount of the long-chain branch is too large and therefore, the mechanical strength decreases.

For the control thereof, it is important to reduce the change in the monomer or comonomer concentration during polymerization or in the polymerization temperature by using the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound. Production of the long-chain branch also depends on the polymerization solvent, and selection of the above-described hydrocarbon solvent is important. The solubility of the copolymer for a solvent is considered to affect the production of the long-chain branch, and the control can be effected also by selecting the comonomer content and the solvent species. In the case of a solvent for which the polymer has high solubility and in a copolymer having a high comonomer content, the phase angle $\delta(G^*=0.1 \text{ MPa})$ tends to become large, and the phase angle $\delta(G^*=0.1 \text{ MPa})$ can be made small, for example, by using hexane or the like for which the polymer has low solubility.

As a characteristic feature of the copolymer of the present invention, the difference T90–T10 (° C.) between the temperature T10 (° C.) allowing 10 wt % of the total to elute in an integrated elution curve as determined by the continuous temperature rising elution fractionation method (TREF) and the temperature T90 (° C.) allowing 90 wt % of the total to elute and the weight average elution temperature Tw (° C.) preferably satisfy the following relationship:

$$28-0.3 \times Tw \leq T90-T10 \leq 41-0.3 \times Tw$$

T90–T10 is a parameter indicating the width of the composition distribution and as regards the control method, the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, is less susceptible to deterioration of the active site even in the presence of a polar monomer and maintains homogeneous active species, so that a polymer having homogeneous molecular chains can be produced. Furthermore, by reducing the change in the temperature or the monomer or comonomer concentration during the polymerization, a copolymer with a narrow molecular weight distribution can be produced.

MFR of the copolymer of the present invention is preferably from 0.01 to 100, more preferably from 0.02 to 30, still more preferably from 0.05 to 10. If MFR is less than 0.01, moldability is poor, whereas if it exceeds 100, the strength decreases.

As regards the control method therefor, MFR can be increased/decreased by raising/lowering the polymerization temperature or can also be controlled by the above-described normal molecular weight controlling method. Furthermore, in use of the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, MFR can be controlled by controlling the structures of $R^1$ to $R^4$.

As additional conditions for attaining the objects of the present invention, the total amount of branches except for branch structures derived from the side chain substituent represented by $R^{17}$ in the formula above of the α-olefin as the component (a) and the $CO_2(R^{19})$ group of the (meth)acrylic acid (or ester) as the component (b) is preferably $1/1,000$ C or less.

As regards the control method therefore, in the use of the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, the total amount of branches can be controlled by controlling the selection of $R^1$ to $R^4$. The total amount of branches can be also increased/decreased by raising/lowering the polymerization temperature.

Out of (meth)acrylic acid (or ester) monomer units forming the ternary copolymer of ethylene-α olefin-(meth)acrylic acid (or ester) of the present invention, the amount of (meth)acrylic acid (or ester) monomer units present in the terminal of the copolymer is preferably 20% or less, more preferably 5% or less, still more preferably 1% or less, based on the amount of all (meth)acrylic acid (or ester) monomer units contained in the copolymer, and it is preferred that a (meth)acrylic acid (or ester) monomer unit is substantially not present in the terminal.

As regards the control method therefor, in the use of the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, the control can be effected by selecting the structures of $R^1$ to $R^4$.

The copolymer of the present invention preferably contains no heterogeneous bond based on 1,2-insertion.

As regards the control method therefor, in the use of the above-described α-olefin polymerization catalyst containing a component obtained by reacting the specific triarylphosphine compound, particularly a component where either one of $R^1$ and $R^2$ and either one of $R^3$ and $R^4$ are a secondary alkyl group, with a Group 10 transition metal compound, particularly a Pd compound, the control can be effected by selecting the structures of $R^1$ to $R^4$.

EXAMPLES

The present invention is described in greater detail by referring to Examples and Comparative Examples, and the configurations of the present invention are verified to have reasonableness, significance and superiority to conventional techniques by the data in preferred Examples and the comparison of Examples with Comparative Examples. The structures of ligands used in Examples and Comparative Examples are shown in Table 1.

TABLE 1

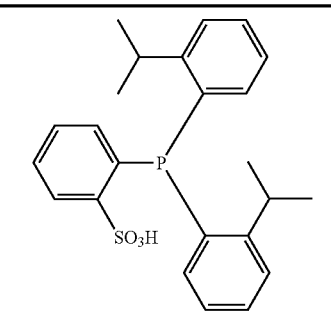

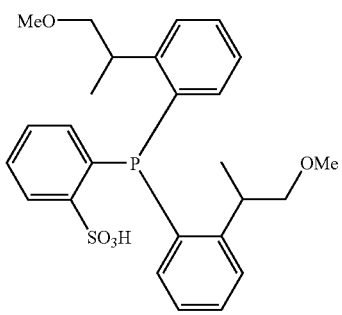 [SMILES: COCC(C)c1ccccc1P(c1ccccc1C(C)COC)c1ccccc1S(=O)(=O)O]

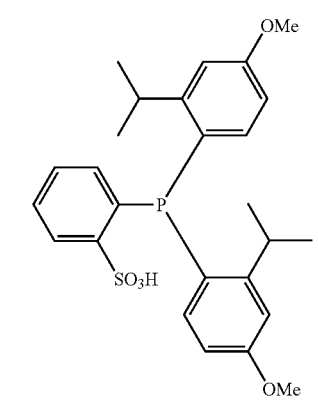 [SMILES: COc1ccc(P(c2ccc(OC)cc2C(C)C)c2ccccc2S(=O)(=O)O)c(C(C)C)c1]

TABLE 1-continued

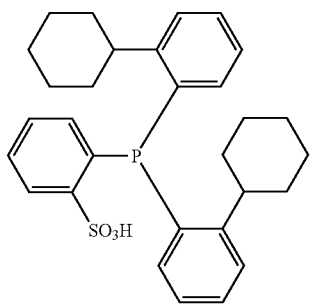 [SMILES: O=S(=O)(O)c1ccccc1P(c1ccccc1C1CCCCC1)c1ccccc1C1CCCCC1]

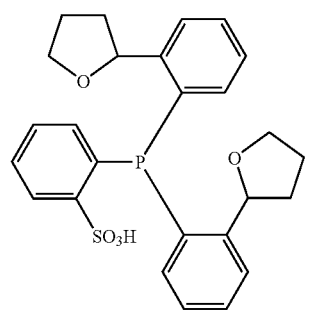 [SMILES: O=S(=O)(O)c1ccccc1P(c1ccccc1C1CCCO1)c1ccccc1C1CCCO1]

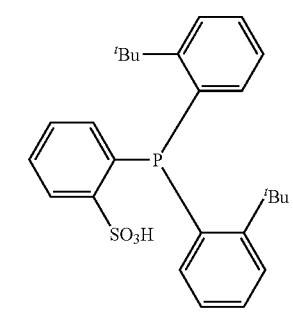 [SMILES: CC(C)(C)c1ccccc1P(c1ccccc1C(C)(C)C)c1ccccc1S(=O)(=O)O]

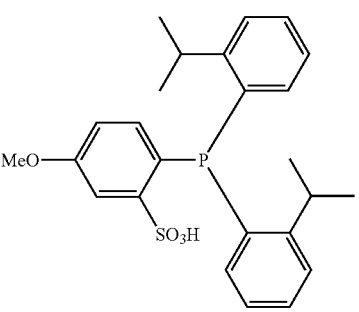 [SMILES: COc1ccc(P(c2ccccc2C(C)C)c2ccccc2C(C)C)c(S(=O)(=O)O)c1]

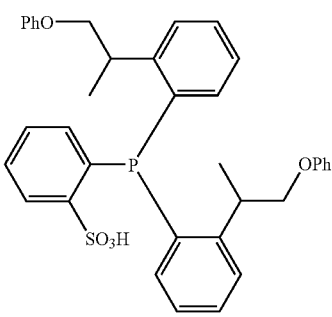 [SMILES: CC(COc1ccccc1)c1ccccc1P(c1ccccc1C(C)COc1ccccc1)c1ccccc1S(=O)(=O)O]

TABLE 1-continued

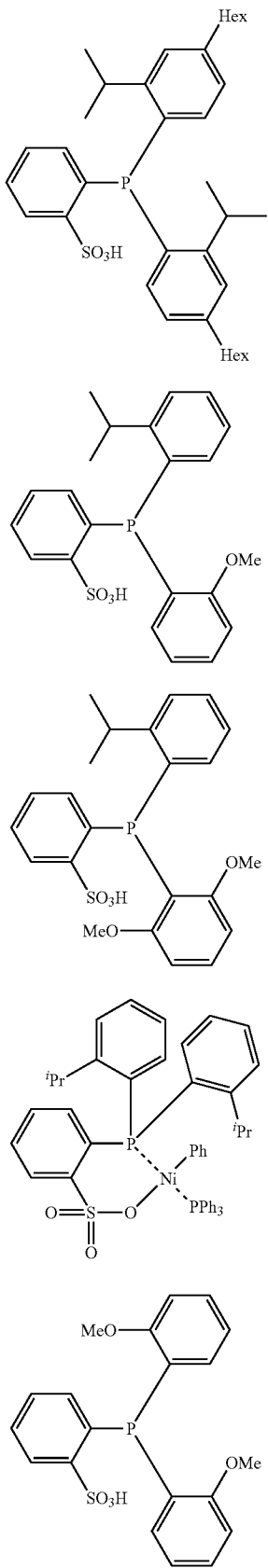

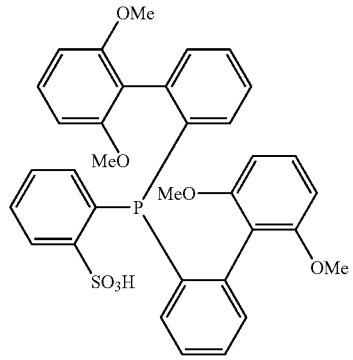 [SMILES: COc1cccc(OC)c1-c1ccccc1P(c1ccccc1-c1c(OC)cccc1OC)c1ccccc1S(=O)(=O)O]

Also, in Examples, the following abbreviations were used.
Pd(dba)$_2$: Bis(dibenzilideneacetone)palladium
Ni(cod)$_2$: Bis(cyclooctadiene)nickel
MA: Methyl acrylate
EA: Ethyl acrylate
tBA: Tertiary-butyl acrylate
MMA: Methyl methacrylate
AA: Acrylic acid
VA: Vinyl acetate
LUA: Lauryl acrylate
HEA: 2-Hydroxyethyl acrylate
EUA: Ethyl undecylenate
NBMOH: (5-Norbornene)-2-methanol
NBYA: (5-Norbornen)-2-yl acetate
ATMS: Allyltriethoxysilane
BTOH: (3-Buten)-1-ol
TPB: Triphenylborane
clay: Sulfuric acid/lithium sulfate-treated montmorillonite 1. Evaluation Method
(1) Molecular Weight and Molecular Weight Distribution (Mw, Mn, Q Value)
(Measurement Conditions)
Model of apparatus used: 150C manufactured by Waters Corp., detector: MIRAN 1A•IR Detector manufactured by FOXBORO (measurement wavelength: 3.42 μm), measurement temperature: 140° C., solvent: orthodichlorobenzene (ODCB), column: AD806M/S (three columns) manufactured by Showa Denko K.K., flow rate: 1.0 mL/min, amount injected: 0.2 mL.
(Preparation of Sample)
As the sample, a 1 mg/mL solution was prepared using ODCB (containing 0.5 mg/mL of BHT (2,6-di-tert-butyl-4-methylphenol)) and dissolving it at 140° C. over about 1 hour.
(Calculation of Molecular Weight)
The calculation was performed by the standard polystyrene method, and the conversion from retention volume to molecular weight was performed using a previously prepared calibration curve with standard polystyrenes.
The standard polystyrenes used all are brand names of Tosoh Corporation, that is, F380, F288, F128, F80, F40, F20, F10, F4, F1, A5000, A2500 and A1000. A solution was prepared by dissolving each standard polystyrene in ODCB (containing 0.5 mg/mL of BHT) to have a concentration of 0.5 mg/mL, and 0.2 mL of the solution was injected to prepare a calibration curve. The calibration curve employs a cubic expression obtained by approximation using the least squares method. For the viscosity equation ($[\eta]=K \times M^\alpha$) used in the conversion to molecular weight, the following numerical values were used.
PS: $K=1.38 \times 10^{-4}$, $\alpha=0.7$
PE: $K=3.92 \times 10^{-4}$, $\alpha=0.733$
PP: $K=1.03 \times 10^{-4}$, $\alpha=0.78$ (2) Melting Point (Tm)

Using a differential scanning calorimeter, DSC6200 manufactured by Seiko Instrument Co., Ltd., 5 mg of the sample strip in a sheet form was packed in the aluminum pan, and the temperature was once raised from room temperature to 200° C. at a temperature rise rate of 100° C./min, held for 5 minutes, then dropped to 20° C. at 10° C./min to effect crystallization, and again raised to 200° C. at 10° C./min, whereby a melting curve was obtained.

The peak top temperature of the main endothermic peak in the final temperature rise stage performed to obtain the melting curve was defined as the melting point Tm and the peak area of the peak was indicated by ΔHm.

(3) Comonomer (α-Olefin, (Meth)acrylic Acid (or Ester)) Content

The comonomer content, that is, the content of α-olefin monomer unit as the component (a) and the content of the (meth)acrylic acid (or ester) monomer unit as the component (b), in the copolymer was measured by the following two methods.

(3-1) Measurement of Comonomer Content by $^{13}$C-NMR

[Preparation of Sample]

About 250 mg of the sample formed into a film shape of about 100 μm in thickness was weighed in a test tube having an outer diameter of 10 mm, and 1.84 ml of ortho-dichlorobenzene and 0.46 ml of deuterated bromobenzene were added. After the upper part of the test tube was purged with nitrogen, the test tube was closed by a lid, and the mixture was heated and dissolved in a high-temperature tank at 130° C. until the sample became uniform.

[$^{13}$C-NMR Measurement]

The measurement was performed using a cryoprobe-equipped NMR measurement device, AVANCE III400, manufactured by Bruker-Biospin under the conditions of gated proton decoupling and no NOE decoupling. The flip angle of the excitation pulse was set to 90°, the pulse interval was set to 16.3 seconds, the measurement temperature was set to 120° C., the cumulated number was set to 500 times or more, and the observed spectrum width was set to 24,038.5 Hz.

Assignments of the $^{13}$C-NMR spectrum were performed by referring to various publications. In the case where the α-olefin is propylene and is hexene and in the case where the polar group-containing vinyl monomer is methyl acrylate and is ethyl acrylate, the partial structures, marks and chemical shifts of the $^{13}$C-NMR resonant peak are shown in Chemical Formulae 9 to 12 below.

[Determination of α-Olefin Content and Polar Group-Containing Vinyl Monomer Content]

The amount $T_E$ proportional to the molar number of the ethylene unit, the amount $T_{\alpha\text{-}0}$ proportional to the molar number of the α-olefin unit, and the molar number $T_F$ of the polar group-containing vinyl monomer unit were determined from the obtained $^{13}$C-NMR spectrum, and the α-olefin content (unit: mol %) and the polar group-containing vinyl monomer content (unit: mol %) were determined according to $T_{\alpha\text{-}0}/(T_E+T_{\alpha\text{-}0}+T_F)\times 100$ and $T_F/(T_E+T_{\alpha\text{-}0}+T_F)\times 100$, respectively.

In the case where the component (a) is propylene and is 1-hexene and in the case where the component (b) is methyl acrylate and is ethyl acrylate, $T_{\alpha\text{-}0}$ and $T_F$ were determined as follows.

[In the Case where the Component (a) is Propylene]

Out of nuclear magnetic resonant peaks produced when propylene was inserted into the chain upon copolymerization, the average value of ½ of the integrated intensity of peaks derived from α methylene carbon in the vicinity of 37.6 ppm and the integrated intensity of peaks derived from methine carbon in the vicinity of 33.2 ppm was determined as the amount $T_{\alpha\text{-}0}$ proportional to the molar number of the propylene unit. $T_{\alpha\text{-}0}=(I_{37.6}/2+I_{33.2})/2$. Here, for example, $I_{37.6}$ is the integrated intensity of peaks derived from α methylene carbon appearing in the vicinity of 37.6 ppm.

[In the Case where the Component (a) is 1-Hexene]

Similarly to propylene, the amount $T_{\alpha\text{-}0}$ proportional to the molar number of the hexene unit was determined using characteristic peaks produced by 1-hexene according to the following formula. $T_{\alpha\text{-}0}=(I_{27.3}/2+I_{34.2}+I_{34.6}/2)/3$. Here, $I_{27.3}$ is the integrated intensity of peaks due to resonance of β methylene appearing in the vicinity of 27.3 ppm by the copolymerization of 1-hexene, $I_{34.2}$ is the integrated intensity of resonant peaks attributable to the fourth carbon counting from the branch end of the butyl branch produced by the copolymerization of 1-hexene, and $I_{34.6}$ is the integrated intensity of peaks due to resonance of α methylene.

[In the Case where the Component (b) is Methyl Acrylate]

Out of nuclear magnetic resonance signals produced due to copolymerization of methyl acrylate, the average value of half of the integrated intensity of β methylene carbon in the vicinity of 27.8 ppm, half of the integrated intensity of α methylene carbon in the vicinity of 32.8 ppm, and the integrated intensity of methine carbon in the vicinity of 46.0 ppm was determined as the amount ($T_F$) proportional to the molar number of the methyl acrylate unit. $T_F=(I_{27.8}/2+I_{32.8}/2+I_{46.0})/3$.

[In the Case where the Component (b) is Ethyl Acrylate]

Similarly to methyl acrylate, out of nuclear magnetic resonance signals produced due to copolymerization of ethyl acrylate, the average value of half of the integrated intensity of β methylene carbon in the vicinity of 27.8 ppm, half of the integrated intensity of α methylene carbon in the vicinity of 32.8 ppm, and the integrated intensity of methine carbon in the vicinity of 46.0 ppm was determined as the amount ($T_F$) proportional to the molar number of the ethyl acrylate unit. $T_F=(I_{27.8}/2+I_{32.8}/2+I_{46.0})/3$. Incidentally, the amount $T_E$ proportional to the molar number of the ethylene unit was determined as a value obtained by adding half of the integrated intensity of all α methylene carbon peaks produced by the above-described respective comonomers and the integrated intensity of all β methylene carbon peaks to the integrated intensity of main peaks including γ methylene in the vicinity of 30 ppm, and multiplying the resulting value by ½. $T_E=(I_{30}+I_\alpha/2+I_\beta)/2$. Here, $I_{30}$ is the integrated intensity of main peaks including γ methylene in the vicinity of 30 ppm, and $I_{\alpha 0}$ is $I_{37.6}+I_{32.8}$ when the comonomers are propylene and methyl acrylate, and $I_{34.6}+I_{32.8}$ when the comonomers are 1-hexene and ethyl acrylate.

[Total Amount of Branches Except for Branch Structures Derived from the Copolymerized α-Olefin and Polar Group-Containing Vinyl Monomer]

A $^{13}$C-NMR spectral analysis was performed by referring to *Macromolecules*, 32(5), 1620 (1999) and while attribution of branch structures except for branch structures derived from the copolymerized α-olefin and polar group-containing vinyl monomer was performed, the amount of those branches per 1.000 carbon and the sum total thereof were determined by a known method.

Structure of Propylene Unit-Inserted Moiety and Marks

The value in the parenthesis is the chemical shift value of the characteristic peak of 13C-NMR.

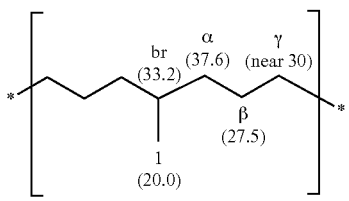

Structure of 1-Hexene Unit-Inserted Moiety and Marks

The value in the parenthesis is the chemical shift value of the characteristic peak of 13C-NMR.

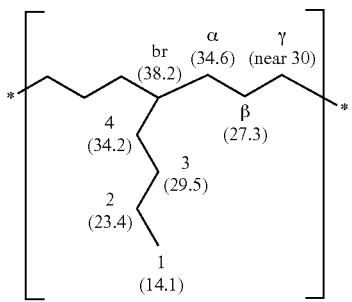

Structure of Ethyl Acrylate Unit-Inserted Moiety and Marks

The value in the parenthesis is the chemical shift value of the characteristic peak of 13C-NMR.

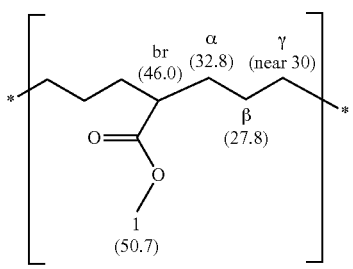

Structure of Ethyl Acrylate Unit-Inserted Moiety and Marks

The value in the parenthesis is the chemical shift value of the characteristic peak of 13C-NMR.

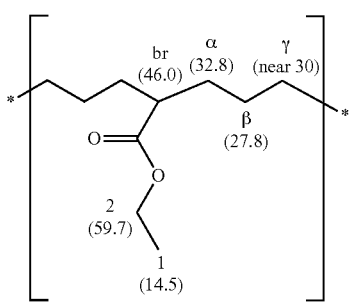

(3-2) Measurement of (Meth)Acrylic Acid (or Ester) Monomer Content by IR

As the analysis sample, a press plate of about 0.5 mm was produced, and its infrared absorption spectrum was obtained using Model FTIR-8300 manufactured by Shimadzu Corporation. The comonomer content was calculated based on the overtone absorption of carbonyl group in the vicinity of 3,450 $cm^{-1}$ and the infrared absorption intensity ratio of olefin absorption in the vicinity of 4,250 $cm^{-1}$. For the calculation, a calibration curve prepared by the $^{13}C$-NMR measurement above was used.

In the present invention, the above-described two kinds of method are employed. The analysis by IR is a simple method but the analysis accuracy is relatively low compared with the analysis by $^{13}C$-NMR. In Examples of the present invention, when values of both analyses are present, the analysis value by $^{13}C$-NMR is employed.

(4) Composition Distribution Measurement by TREF

The measurement was performed using an apparatus manufactured by Japan Polyethylene Corp. by the following procedure under the following conditions.

(4-1) Sample

The sample (20 mg) and 20 mL of o-dichlorobenzene were weighed in 20 mL-volume vial, and the vial was closed by a metal-made screw cap and then placed in a dry bath kept at 140° C. The mixture was dissolved for 2 hours while stirring by hand every 15 minutes and after the completion of dissolution, the absence of insoluble components was confirmed with an eye.

(4-2) Deposition

Deposition was performed using an apparatus where a 400 W heater and a thermocouple are attached to an aluminum block processed to gaplessly house a stainless steel column having an inner diameter of 8 mm and a length of 120 mm (manufactured by Japan Polyethylene Corp.). The column was previously packed with glass beads and kept at 140° C. in the apparatus above. The sample solution at 140° C. was injected thereinto and subsequently, the aluminum block housing the column was cooled to room temperature at a rate of 4° C./h, whereby the sample was deposited on the glass bead.

(4-3) Elution

The elution was performed using an apparatus where a Peltier device, a 200 W heater and a thermocouple are attached to an aluminum block processed to gaplessly house a stainless steel column having an inner diameter of 8 mm and a length of 120 mm and a stainless steel tube having an outer diameter of 1/16 inches and being connected to the column (manufactured by Japan Polyethylene Corp.). An infrared spectrometer, MIRAN Model 1A, equipped with a pump for LC, Model L-6200, manufactured by Hitachi Ltd, a thermally insulated lead pipe and a liquid flow cell was connected to the apparatus to fabricate a system where the amount of the sample in a solvent can be measured by flowing the solvent at a constant flow rate while heating the column at a constant rate. The column after the completion of deposition was housed in the system, the measurement wavelength of the infrared spectrometer was set to 3.42 μm, o-dichlorobenzene was flowed at a flow rate of 1.0 mL/min for about 30 minutes at 20° C., and the base line was stabilized. Subsequently, while flowing o-dichlorobenzene at a flow rate of 1.0 mL/min, the temperature was raised to 130° C. at a rate of 50° C./h, and the temperature during this period and the output of the infrared spectrometer were recorded by a computer. The obtained chromatogram was processed to obtain an elution temperature-elution amount curve. Incidentally, when the elution starting temperature apparently fell below 20° C., the temperature was dropped to 0° C. at a rate of 4° C./h without flowing o-dichlorobenzene before the elution operation, then o-dichlorobenzene was flowed at a flow rate of 1.0 mL/min for about 30 minutes at 0° C. and after the base line was stabilized, while flowing o-dichlorobenzene at a flow rate of 1.0 mL/min, the temperature was raised to 130° C. at a rate of 50° C./h, whereby the measurement was performed. From the data obtained, the weight average elution temperature Tw was calculated according to the following formula.

$$Tw = \frac{\sum I(T) \times T}{\sum I} \qquad \text{[Math. 1]}$$

Here, T represents the elution temperature and I(T) represents the elution amount at a temperature T (° C.). Also, T90 and T10 are the elution temperatures at elution amounts of 90 wt % and 10 wt %, respectively, based on the total.

(5) Measurement of $\delta(G^*=0.1$ MPa) by Dynamic Viscoelasticity Measurement

The resin tested was press-molded at 160° C. into a circular form of 25 mm in diameter and 1 mm in thickness, and this was used as the sample. As the apparatus for measuring the dynamic viscoelastic characteristics, a rotary rheometer, Model ARES, manufactured by Rheometrics and a parallel plate of 25 mm in diameter were used. The dynamic viscoelasticity was measured in a nitrogen atmosphere under the following conditions.

Temperature: 160° C.
Distortion amount: 10%
Measurement angular frequency range: $1.0 \times 10^{-2}$ to $1.0 \times 10^2$ rad/s
Measurement interval: 5 points/decade The phase angle $\delta$ was plotted with respect to the common logarithm logG* of the complex modulus G*(Pa), and the value of $\delta$ (°) at a point corresponding to logG*=5.0 was determined as $\delta(G^*=0.1$ MPa). In the case where the measurement points lacked the point corresponding to logG*=5.0, the $\delta$ value at logG*=5.0 was determined by linear interpolation using two points before and after logG*=5.0. Also, when logG*<5 in all of the measurement points, the $\delta$ value at logG*=5.0 was determined by extrapolation of the quadratic curve using the values at three points from the larger logG* value side.

(6) Measurement of tensile modulus, tensile yield stress, nominal tensile stress at break and nominal tensile strain at break by tensile test A small test piece of form 5B described in JIS K7162 obtained by preparing a sheet of 1 mm in thickness by the method described in JIS K7151 (Cooling Method A) from the ethylene-based copolymer of each Example and punching the sheet was subjected to a tensile test under the conditions of a tensile speed of 10 mm/min and a temperature of 23° C., and from the obtained stress-strain curve, the tensile modulus, tensile yield stress, nominal tensile stress at break and nominal tensile strain at break were calculated by the method described in *Seikei Kakou* (*Molding Process*), Vol. 4, No. 8, pp. 489-496 (1992). Incidentally, the tensile yield stress was assigned to the true stress at the maximum point when a distinct maximum point is present in the nominal stress-strain curve, and assigned to the true stress at the inflection point in the true stress-true strain curve when such a maximum point is lacking. For the calculation of strain, a displacement between chucks was used.

(7) Tensile Impact Strength

A test piece of form 4 described in JIS K7160 was produced by preparing a sheet of 1 mm in thickness by the method described in JIS K7151 (Cooling Method A) from the ethylene-based copolymer of each Example and punching the sheet, and the measurement was performed by using this test piece under the conditions described in JIS K7160.

(8) Wettability Test

A sheet of 1 mm in thickness was prepared by the method described in JIS K7151 (Cooling Method A), and the sheet was dipped in ethanol contained in a beaker and then subjected to ultrasonic washing for 1 minute. After lightly wiping off the ethanol with gauze, an about 1 cm-square character was written on the surface thereof by using an aqueous felt pen "RIB" MyT-7 produced by Mitsubishi Pencil Co., Ltd., and the wettability was judged by the shape of the character after 10 seconds. The criteria of A, B, C and D are as follows.

A: Liquid was not or scarcely repelled and the outline of the character is clear.

B: Liquid was slightly repelled, but the line of the character was scarcely broken.

C: Liquid was repelled, and the line of the character was broken in spots.

D: Liquid was strongly repelled, and the line of the character was broken everywhere.

2. Synthesis of Ligand

Ligands obtained in Synthesis Examples below were used. In the following Synthesis Examples, unless otherwise indicated, the operation was performed in a purified nitrogen atmosphere, and the solvent was used after its dehydration and deoxidation.

Synthesis Example 1

Synthesis of Ligand (I)

A n-butyllithium hexane solution (2.5 M, 2 mL, 5 mmol) was slowly added dropwise to a tetrahydrofuran (20 mL) solution of anhydrous benzenesulfonic acid (400 mg, 2.5 mmol) at 0° C. The solution was stirred for 1 hour while raising the temperature to room temperature. The reaction solution was cooled to −70° C. and after adding phosphorus trichloride (340 mg, 2.5 mmol), this mixture was stirred for 2 hours while raising the temperature to room temperature (Reaction Solution A).

A n-butyllithium hexane solution (2.5 M, 2 mL, 5 mmol) was slowly added dropwise to a diethyl ether (20 mL) solution of 1-bromo-2-isopropylbenzene (1 g, 5 mmol) at −30° C. The mixed solution was stirred for 3 hours while raising the temperature to room temperature. The solution was added dropwise to Reaction Solution A at room temperature, and the mixed solution was stirred for one night. After the reaction, water (20 mL) was added, and the resulting solution was extracted with ether (20 mL×2) and washed with 1 N hydrochloric acid (20 mL×2). Thereafter, the solvent was removed by evaporation, and the residue was washed with methanol (5 mL) to obtain 100 mg of the target product as a white product.

1H NMR (CDCl3, ppm/d): 8.35 (ddd, J=0.8, 4.8, 7.6 Hz, 1H), 7.74 (tt. J=1.4, 7.6 Hz, 1H), 7.65 (t, J=7.6 Hz, 2H), 7.53 (t, J=6.4 Hz, 2H), 7.42 (ddt, J=1.2, 2.8, 7.6 Hz, 1H), 7.26 (ddt, J=0.8, 4.8, 8.0 Hz, 2H), 7.05 (dd, J=0.8, 7.6 Hz, 1H), 6.98 (dd, J=0.8, 5.2 Hz, 2H), 3.00 (m, 2H), 1.15 (d, J=6.8 Hz, 6H), 1.09 (d, J=6.0 Hz, 6H). 31P NMR (CDCl3, ppm/d): 9.5.

Synthesis Example 2

Synthesis of Ligand (II)

A n-butyllithium hexane solution (2.5 M, 1.9 mL, 4.8 mmol) was slowly added dropwise to a tetrahydrofuran (10 mL) solution of anhydrous benzenesulfonic acid (400 mg, 2.5 mmol) at 0° C. The mixed solution was stirred for 1 hour while raising the temperature to room temperature. The reaction solution was cooled to −78° C. and after adding phosphorus trichloride (0.2 mL, 2.4 mmol), this mixture was stirred for 2 hours (Reaction Solution B).

A n-butyllithium hexane solution (2.5 M, 1.9 mL, 4.8 mmol) was added dropwise to a tetrahydrofuran (10 mL) solution of 1-bromo-2-(1'-methoxymethyl)ethylbenzene (1 g, 4.8 mmol) at 0° C. The mixed solution was stirred for 1 hour while raising the temperature to room temperature. The obtained solution was added dropwise to Reaction Solution B at 0° C., and the mixed solution was stirred at room temperature for 3 hours. After removing the solvent by evaporation, water (100 mL) was added, and the resulting solution was made acidic (PH<3) by adding hydrochloric acid, then extracted with methylene chloride (100 mL×3) and dried over sodium sulfate. Thereafter, the solvent was removed by evaporation, and the residue was recrystallized from ethyl acetate/diethyl ether (1/10) to obtain the target product as a white product.

1H NMR (CDCl3, ppm/d): 8.30 (br, 1H), 7.60 (br, 3H), 7.50 (br, 2H), 7.40 (br, 1H), 7.27 (br, 2H), 7.04 (br, 3H), 3.0 (br, 12H), 1.1 (br, 6H). 31P NMR (CDCl3, ppm/d): −8.5.

Synthesis Example 3

Synthesis of Ligand (III)

A n-butyllithium hexane solution (2.5 M, 17.4 mL, 43.6 mmol) was slowly added dropwise to a tetrahydrofuran (200 mL) solution of anhydrous benzenesulfonic acid (3.4 g, 21.8 mmol) at 0° C. The mixed solution was stirred for 1 hour while raising the temperature to room temperature. The reaction solution was cooled to −78° C. and after adding phosphorus trichloride (1.9 mL, 21.8 mmol), this mixture was stirred for 2 hours (Reaction Solution C).

A tert-butyllithium hexane solution (1.6 M, 54.5 mL, 87.2 mmol) was slowly added dropwise at −78° C. to a tetrahydrofuran (200 mL) solution of 1-bromo-2-isopropyl-4-methoxybenzene (10 g, 43.6 mmol), and the mixed solution was stirred for 1 hour. The obtained solution was added dropwise to Reaction Solution C at −78° C., and the mixed solution was stirred at room temperature for one night. After removing the solvent by evaporation, water (200 mL) was added, and the resulting solution was made acidic (PH<3) by adding hydrochloric acid, then extracted with methylene chloride (100 mL×3) and dried over sodium sulfate. Thereafter, the solvent was removed by evaporation, and the residue was recrystallized from methanol to obtain 0.3 g of the target product as a white product.

1H NMR (CDCl3, ppm/d): 8.34 (dd, J=5.2, 7.6 Hz, 1H), 7.71 (t, J=7.6 Hz, 1H), 7.40 (m, 1H), 7.1-7.0 (m, 3H), 6.91 (dd, J=8.8, 14.4 Hz, 2H), 6.75 (d, J=8.4 Hz, 2H), 3.80 (s, 6H), 2.97 (m, 2H), 1.15 (d, J=6.8 Hz, 6H), 1.08 (br, 6H). 31P NMR (CDCl3, ppm/d: −10.7.

Synthesis Example 4

Synthesis of Ligand (IV)

A n-butyllithium hexane solution (2.5 M, 10 mL, 25.3 mmol) was slowly added dropwise to a tetrahydrofuran (50 mL) solution of anhydrous benzenesulfonic acid (2 g, 12.6 mmol) at 0° C. The mixed solution was stirred for 1 hour while raising the temperature to room temperature. The reaction solution was cooled to −78° C. and after adding phosphorus trichloride (1.0 mL, 12.6 mmol), this mixture was stirred for 2 hours (Reaction Solution D).

A tert-butyllithium hexane solution (1.6 M, 31.6 mL, 50.6 mmol) was slowly added dropwise at 0° C. to a tetrahydrofuran (50 mL) solution of 1-bromo-2-cyclohexylbenzene (6 g, 25.3 mmol), and the mixed solution was stirred for 1 hour. The obtained solution was added dropwise to Reaction Solution D at −78° C., and the mixed solution was stirred at room temperature for one night. LC-MS Purity: 50%. After adding water (200 mL), the resulting solution was made acidic (PH<3) by adding hydrochloric acid, then extracted with methylene chloride (100 mL×3) and dried over sodium sulfate. Thereafter, the solvent was removed by evaporation, and the residue was purified by silica gel column chromatography (dichloromethane/methanol=50/1) to obtain 1.0 g of the target product as a white product.

1H NMR (CDCl3, ppm/d): 7.86 (m, 1H), 7.30 (dt, J=1.2, 7.6 Hz, 1H), 7.24-7.15 (m, 5H), 6.96 (m, 2H), 6.83 (m, 1H), 6.57 (m, 2H), 3.21 (br, 2H), 1.55 (br, 8H), 1.31 (br, 4H), 1.14 (br, 8H). 31P NMR (CDCl3, ppm/d): −28.7.

Synthesis Example 5

Synthesis of Ligand (V)

A n-butyllithium hexane solution (2.5 M, 4.6 mL, 11.5 mmol) was slowly added dropwise to a tetrahydrofuran (20 mL) solution of anhydrous benzenesulfonic acid (0.9 g, 5.8 mmol) at 0° C. The mixed solution was stirred for 1 hour while raising the temperature to room temperature. The reaction solution was cooled to −78° C. and after adding phosphorus trichloride (0.5 mL, 5.8 mmol), this mixture was stirred for 2 hours at 0° C. (Reaction Solution E).

A tert-butyllithium hexane solution (1.5 M, 15.4 mL, 23 mmol) was added dropwise at 0° C. to a tetrahydrofuran (50 mL) solution of 1-bromo-2-hydrofurylbenzene (2.6 g, 11.5 mmol), and the mixed solution was stirred for 1 hour. The obtained solution was added dropwise to Reaction Solution E at −50° C., and the mixed solution was stirred at room temperature for one night. After removing the solvent by evaporation, water (100 mL) was added, and the resulting solution was washed with MTBE (100 mL×3), made acidic (PH<3) by adding hydrochloric acid, then extracted with methylene chloride (100 mL×3) and dried over sodium sulfate. Thereafter, the solvent was removed by evaporation, and the residue was washed with methanol to obtain 1.0 g of the target product as a white product.

1H NMR (DMSO, ppm/d): 7.88 (m, 3H), 7.42 (m, 2H), 7.37-7.29 (m, 3H), 7.22 (t, J=7.4 Hz, 1H), 7.11 (t, J=7.4 Hz, 2H), 6.72 (m, 1H), 6.63 (m, 2H), 5.27 (br, 2H), 3.94 (m, 2H), 3.67 (m, 2H), 2.0-1.1 (br, 8H). 31P NMR (CDCl3, ppm/d): −30.4.

Synthesis Example 6

Synthesis of Ligand (VI)

A n-butyllithium hexane solution (2.5 M, 11.6 mL, 29 mmol) was slowly added dropwise to a tetrahydrofuran (100 mL) solution of anhydrous benzenesulfonic acid (2.3 g, 14.5 mmol) at 0° C. The mixed solution was stirred for 1 hour while raising the temperature to room temperature. The reaction solution was cooled to −78° C. and after adding phosphorus trichloride (1.26 mL, 14.5 mmol), this mixture was stirred for 2 hours (Reaction Solution F).

A n-butyllithium hexane solution (1.6 M, 11.6 mL, 29 mmol) was added dropwise at 0° C. to a diethyl ether (100 mL) solution of 1-bromo-2-tert-butylbenzene (6.2 g, 29 mmol), and the mixed solution was stirred for 1 hour. The obtained solution was added dropwise to Reaction Solution F at −78° C., and the mixed solution was stirred at room temperature for one night. After removing the solvent by evaporation, water (100 mL) was added, and the resulting solution was made acidic (PH<3) by adding hydrochloric acid, then extracted with methylene chloride (100 mL×3) and dried over sodium sulfate. Thereafter, the solvent was removed by evaporation, and the residue was recrystallized from methanol to obtain 3.5 g of the target product as a white product.

1H NMR (CDCl3, ppm/d): 8.33 (dd, J=5.2, 7.6 Hz, 1H), 7.7 (m, 3H), 7.62 (t, J=7.6 Hz, 1H), 7.55 (t, J=7.6 Hz, 1H), 7.38 (m, 1H), 7.25 (t, J=7.6 Hz, 1H), 7.2-7.1 (m, 3H), 6.90 (dd, J=8.0, 14.0 Hz, 1H), 1.37 (s, 9H), 1.34 (s, 9H). 31P NMR (CDCl3, ppm/d): 4.5.

Synthesis Example 7

Synthesis of Ligand (VII)

A n-butyllithium hexane solution (2.5 M, 4.7 mL, 11.8 mmol) was slowly added dropwise to a diethyl ether (10 mL) solution of 1-bromo-2-isopropylbenzene (2.34 g, 11.8 mmol) at −30° C. The mixed solution was stirred for 2 hours while raising the temperature to room temperature. The reaction solution was added to a tetrahydrofuran solution of phosphorus trichloride (0.81 g, 5.88 mmol) at −78° C., and the mixed solution was stirred for 2 hours at the same temperature (Reaction Solution G).

A tert-butyllithium hexane solution (1.6 M, 5.9 mL, 9.4 mmol) was slowly added dropwise at −78° C. to a tetrahydrofuran (12 mL) solution of 1-bromo-2-sulfonic acid isopropyl ester-4-methoxybenzene (1.5 g, 4.7 mmol), and the mixed solution was stirred for 4 hours. The obtained solution was added dropwise to Reaction Solution G at −78° C., and the mixed solution was stirred at room temperature for one night. After adding water (20 mL), the resulting solution was made acidic (PH<2) by adding hydrochloric acid, then extracted with methylene chloride (50 mL×3), washed with an aqueous sodium chloride solution and dried over sodium sulfate. Thereafter, the solvent was removed by evaporation (yield: 1.2 g). This product was dissolved in methanol (8 mL), and an aqueous sodium hydroxide solution (1 M, 4 mL, 4 mmol) and tetrahydrofuran (8 mL) was added thereto. The resulting mixture was stirred at 50° C. for 4 hours and after adding 2 N hydrochloric acid (20 mL), the solution was extracted with methylene chloride (50 mL×3) and dried over sodium sulfate. Subsequently, the solvent was removed by evaporation, and the residue was washed with a small amount of diethyl ether to get the target product as a white product (yield: 0.3 g).

1H NMR (CDCl3, ppm/d): 7.94 (br, 1H), 7.68 (m, 2H), 7.59 (m, 2H), 7.31 (m, 2H), 7.04 (m, 2H), 6.94 (d, J=2.8 Hz, 2H), 3.95 (s, 3H), 3.06 (m, 2H), 1.19 (m, 12H). 31P NMR (CDCl3, ppm/d): −10.4.

Synthesis Example 8

Synthesis of Ligand (VIII)

A n-butyllithium hexane solution (2.5 M, 5 mL, 12.6 mmol) was slowly added dropwise to a tetrahydrofuran (20 mL) solution of anhydrous benzenesulfonic acid (1 g, 6.3 mmol) at 0° C. The mixed solution was stirred for 1 hour while raising the temperature to room temperature. The reaction solution was cooled to −78° C. and after adding phosphorus trichloride (0.54 mL, 6.3 mmol), this mixture was stirred for 2 hours (Reaction Solution H).

A n-butyl lithium hexane solution (2.5 M, 5.0 mL, 12.6 mmol) was slowly added dropwise at 0° C. to a diethyl ether (20 mL) solution of 1-bromo-2-(1'-methyl-2'-phenoxy)ethylbenzene (3.8 g, 12.6 mmol), and the mixed solution was stirred for 2 hours at room temperature. The obtained solution was added dropwise to Reaction Solution H at room temperature, and the mixed solution was stirred at room temperature for one night. LC-MS Purity: 22%. After adding water, the resulting solution was made acidic (PH<3) by adding hydrochloric acid, then extracted with methylene chloride (100 mL×3) and dried over sodium sulfate. Thereafter, the solvent was removed by evaporation, and the residue was purified by silica gel column chromatography (dichloromethane/methanol=70/1) to obtain 2.0 g of the target product as a white product.

1H NMR (DMSO, ppm/d): 8.34 (t, J=6.0 Hz, 1H), 7.70 (t, J=7.6 Hz, 1H), 7.40 (m, 1H), 7.4-7.0 (m, 10H), 6.9-6.5 (m, 9H), 4.0 (m, 2H), 3.7 (m, 4H), 1.1 (m, 3H), 0.8 (m, 3H). 31P NMR (CDCl3, ppm/d): −29.9.

Synthesis Example 9

Synthesis of Ligand (IX)

A n-butyllithium hexane solution (2.5 M, 3 mL, 7.6 mmol) was slowly added dropwise to a tetrahydrofuran (10 mL) solution of anhydrous benzenesulfonic acid (0.6 g, 3.8 mmol) at 0° C. The mixed solution was stirred for 1 hour while raising the temperature to room temperature. The reaction solution was cooled to −78° C. and after adding phosphorus trichloride (0.33 mL, 3.8 mmol), this mixture was stirred for 2 hours (Reaction Solution I).

A n-butyl lithium hexane solution (2.5 M, 3.0 mL, 7.6 mmol) was slowly added dropwise at 0° C. to a diethyl ether (20 mL) solution of 1-bromo-2-isopropyl-3-hexylbenzene (2.2 g, 7.6 mmol), and the mixed solution was stirred for 3 hours at room temperature. The obtained solution was added dropwise to Reaction Solution I at −78° C., and the mixed solution was stirred at room temperature for one night. LC-MS Purity: 51%. After adding water, the resulting solution was made acidic (PH<3) by adding hydrochloric acid, then extracted with methylene chloride (50 mL×3) and dried over sodium sulfate. Thereafter, the solvent was removed by evaporation, and the residue was purified by silica gel column chromatography (dichloromethane/methanol=70/1) to obtain 0.8 g of the target product as a white product.

1H NMR (CDCl3, ppm/d): 8.34 (d, J=6.0 Hz, 1H), 7.70 (d, J=7.6 Hz, 1H), 7.40 (m, 1H), 7.29 (d, J=4.4 Hz, 2H), 7.04 (m, 3H), 6.85 (dd, J=7.6, 14.8 Hz, 2H), 2.97 (m, 2H), 2.60 (t, J=7.6 Hz, 4H), 1.54 (m, 4H), 1.25 (s, 12H), 1.2-1.0 (m, 12H), 0.82 (br, 6H). 31P NMR (CDCl3, ppm/d): −9.9.

Synthesis Example 10

Synthesis of Ligand (X)

A n-butyllithium hexane solution (2.5 M, 10 mL, 25.3 mmol) was slowly added dropwise to a tetrahydrofuran (20 mL) solution of anhydrous benzenesulfonic acid (2 g, 12.6 mmol) at 0° C. The mixed solution was stirred for 1 hour while raising the temperature to room temperature. The reaction solution was cooled to −78° C. and after adding phosphorus trichloride (1.0 mL, 12.6 mmol), this mixture was stirred for 2 hours (Reaction Solution J1).

Mg was dispersed in tetrahydrofuran (20 mL) and after adding 1-bromo-2-methoxybenzene (2.3 g, 12.6 mmol), the mixture was stirred for 3 hours at room temperature. The resulting solution was added dropwise to Reaction Solution J1 at −78° C., and the mixture was stirred for 1 hour (Reaction Solution J2).

A n-butyl lithium hexane solution (2.5 M, 5.0 mL, 12.6 mmol) was slowly added dropwise at −30° C. to a diethyl ether (20 mL) solution of 1-bromo-2-isopropylbenzene (2.5 g, 12.6 mmol), and the mixed solution was stirred for 2 hours at room temperature. The obtained solution was added dropwise to Reaction Solution J2 at −78° C., and the mixed solution was stirred at room temperature for one night. LC-MS Purity: 60%. After adding water (50 mL), the resulting solution was made acidic (PH<3) by adding hydrochloric acid, then extracted with methylene chloride (100 mL) and dried over sodium sulfate. Thereafter, the solvent was removed by evaporation, and the residue was recrystallized from methanol to obtain 1.1 g of the target product as a white product.

1H NMR (CDCl3, ppm/d): 8.34 (t, J=6.0 Hz, 1H), 7.7-7.6 (m, 3H), 7.50 (t, J=6.4 Hz, 1H), 7.39 (m, 1 H), 7.23 (m, 1H), 7.1-6.9 (m, 5H), 3.75 (s, 3H), 3.05 (m, 1H), 1.15 (d, J=6.8 Hz, 3H), 1.04 (d, J=6.4 Hz, 3H). 31P NMR (CDCl3, ppm/d): −10.5.

Synthesis Example 11

Synthesis of Ligand (XI)

A n-butyllithium hexane solution (2.5 M, 15.2 mL, 38 mmol) was slowly added dropwise to a tetrahydrofuran (40 mL) solution of anhydrous benzenesulfonic acid (3.0 g, 19 mmol) at 0° C. The mixed solution was stirred for 1 hour while raising the temperature to room temperature. The reaction solution was cooled to −78° C. and after adding phosphorus trichloride (1.7 mL, 19 mmol), this mixture was stirred for 2 hours (Reaction Solution K1).

Isopropylmagnesium chloride (2.0 M, 9.5 mL, 19 mmol) was slowly added dropwise at −40° C. to a tetrahydrofuran (40 mL) solution of 1-iodo-2,6-dimethoxybenzene (5.0 g, 19 mmol), and the mixture was stirred for 2 hours at room temperature. The resulting solution was added dropwise to Reaction Solution K1 at −78° C., and the mixture was stirred for 1 hour at room temperature (Reaction Solution K2).

A n-butyl lithium hexane solution (2.5 M, 7.6 mL, 19.0 mmol) was slowly added dropwise at −30° C. to a diethyl ether (30 mL) solution of 1-bromo-2-isopropylbenzene (3.8 g, 19.0 mmol), and the mixed solution was stirred for 2 hours at room temperature. The obtained solution was added dropwise to Reaction Solution K2 at −78° C., and the mixed solution was stirred at room temperature for one night. LC-MS Purity: 39%. After adding water (60 mL), the resulting solution was made acidic (PH<1) by adding hydrochloric acid, then extracted with methylene chloride (100 mL×3) and dried over sodium sulfate. Thereafter, the solvent was removed by evaporation, and the residue was recrystallized from methanol to obtain 4.4 g of the target product as a white product.

1H NMR (CDCl3, ppm/d): 9.67 (d, J=290.2 Hz, 1H), 8.34 (m, 1H), 7.7-7.5 (m, 3H), 7.50 (m, 1H), 7.41 (m, 1 H), 7.33-7.26 (m, 3H), 6.67 (dd, J=5.2, 8.8 Hz, 2H), 3.65 (s, 6H), 2.97 (m, 1H), 1.14 (d, J=6.8 Hz, 3H), 1.05 (d, J=6.4 Hz, 3H). 31P NMR (CDCl3, ppm/d): −19.1.

Synthesis Example 12

Synthesis of Complex (XII)

Sodium carbonate (0.19 g, 1.75 mmol) was added to a methylene chloride (40 mL) solution of Ligand (I) (0.62 g, 1.45 mmol), and the mixture was stirred for 4 hours at room temperature. The reaction solution was cooled to −20° C. and after adding Ni(PPh3)2(Ph)Cl complex (1.0 g, 1.46 mmol), this mixture was stirred at room temperature for one night. Thereafter, the solvent was removed by evaporation, and the residue was extracted with diethyl ether (10 mL×3) and then recrystallized to obtain 0.9 g of the objective complex.

1H NMR (CDCl3, ppm/d): 8.45-7.07 (m, 32H), 2.29 (m, 2H), 1.24 (m, 12H). 31P NMR (CDCl3, ppm/d): −9.5.

Synthesis Example 13

Synthesis of Ligand (XIII)

A n-butyllithium hexane solution (2.5 M, 25 mL, 62 mmol) was slowly added dropwise to a tetrahydrofuran (60 mL) solution of anhydrous benzenesulfonic acid (5.2 g, 32.9 mmol) at 0° C. The mixed solution was stirred for 20 hours while raising the temperature to room temperature. To this reaction solution, a tetrahydrofuran (20 mL) solution of bis (2-methoxyphenyl)methoxyphosphine (9.1 g, 32.9 mmol) was added dropwise, and the resulting solution was stirred for 16 hours. After adding ammonium chloride (3.4 g, 62 mmol), the solvent was removed by evaporation, and the residue was added with water (100 mL), then washed with MTBE (40 mL×2), made acidic (PH<3) by adding hydrochloric acid, extracted with methylene chloride (60 mL×2), dried over sodium sulfate, and recrystallized at −35° C. to obtain 3.7 g of the target product as a white product.

1H NMR(C2D2Cl4, ppm/d): 6.7-8.2 (m, 12H), 3.79 (s, 6H). 31P NMR (C2D2Cl4, ppm/d): −9.8.

Synthesis Example 14

Synthesis of Ligand (XIV)

A n-butyllithium hexane solution (2.5 M, 3.8 mL, 9.4 mmol) was slowly added dropwise to a tetrahydrofuran (20 mL) solution of anhydrous benzenesulfonic acid (0.74 g, 4.7 mmol) at 0° C. The mixed solution was stirred for 2 hours while raising the temperature to room temperature. The reaction solution was cooled to −78° C. and after adding phosphorus trichloride (0.41 mL, 4.7 mmol), this mixture was stirred for 2 hours at room temperature (Reaction Solution L).

A tert-butyllithium hexane solution (1.5 M, 12.5 mL, 18.8 mmol) was slowly added dropwise at 0° C. to a tetrahydrofuran (25 mL) solution of 1-bromo-2-(2',6'-dimethoxyphenyl)benzene (2.8 g, 9.4 mmol), and the mixed solution was stirred for 30 minutes. The obtained solution was added dropwise to Reaction Solution L at −50° C., and the mixed solution was stirred at room temperature for one night. After removing the solvent by evaporation, water (200 mL) was added, and the resulting solution was made acidic (PH<3) by adding hydrochloric acid, extracted with MTBE (100 mL×3) and dried over sodium sulfate. Thereafter, the solvent was removed by evaporation, and the residue was washed with THF (5 mL) to obtain 0.5 g of the target product as a white product.

1H NMR (CDCl3, ppm/d): 8.08 (m, 1H), 7.61 (m, 3H), 7.42-7.12 (m, 10H), 6.68-6.22 (br, 4H), 3.84-3.31 (br, 9H), 2.96 (br, 3H). 31P NMR (CDCl3, ppm/d): −2.4.

3. Preparation of Chemically Treated Montmorillonite

Treatment Example 1

Preparation of Sulfuric Acid/Lithium Sulfate-Treated Montmorillonite

In a 500 mL-volume three-neck round flask equipped with a stirring blade and a reflux device, 170 g of distilled water was charged and 50 g of 98% sulfuric acid was added dropwise. After setting the internal temperature to 90° C., 30 g of BENCLAY SL (produced by Mizusawa Industrial Chemicals, Ltd.) was added, and the mixture was stirred. Thereafter, reaction was allowed to proceed at 90° C. for 3.5 hours, and the obtained slurry was poured in 150 mL of distilled water, thereby stopping the reaction, filtered by an apparatus with a Nutsche filter and an aspirator connected to a suction bottle, and washed with 75 mL of distilled water. The obtained cake was dispersed in 300 mL of distilled water and after stirring, filtered. This operation was repeated three times.

The recovered cake was added to an aqueous solution prepared by dissolving 17 g of zinc sulfate heptahydrate in 135 mL of pure water in a 1 L-volume beaker and reacted at room temperature for 2 hours, and the obtained slurry was filtered by an apparatus with a Nutsche filter and an aspirator connected to a suction bottle, and washed with 75 mL of distilled water. The obtained cake was dispersed in 300 mL of distilled water and after stirring, filtered. This operation was repeated three times.

The cake was dried at 120° C. all night, as a result, 22 g of a chemically treated form was obtained. This chemically treated montmorillonite was put in a 200 mL-volume flask, dried under reduced pressure at 200° C. and after gas generation was settled, further dried under reduced pressure for 2 hours. After the drying, this was stored in a nitrogen atmosphere. When used for polymerization evaluation, the montmorillonite was slurried with methylene chloride or toluene (40 mg-montmorillonite/ml-solvent) and then added.

Treatment Example 2

Organic Aluminum Treatment of Chemically Treated Montmorillonite

In a flask having an inner volume of 200 mL, 1 g of the dried chemically treated montmorillonite obtained above (Treatment Example 1) was weighed, and 3.6 mL of heptane and 6.4 mL (2.5 mmol) of a heptane solution of triisobutylaluminum were added. This mixture was stirred at room temperature for 1 hour, and the resulting solution was washed with methylene chloride and toluene until a residual liquid ratio of 1/100. The slurry amount was then adjusted to 25 mL by using the same solvent as that finally used for washing.

4. Polymerization (1) [Examples 1-1 to 1-11 and Comparative Examples 1-1 and 1-2]

In a 30 ml-volume flask thoroughly purged with nitrogen, 100 micromol of bis(benzylideneacetone) palladium and phosphorus-sulfonic acid were weighed and dehydrated toluene (10 mL) was added. The mixture was treated by an ultrasonic vibrator for 10 minutes to prepare a catalyst slurry. Subsequently, a 1000 mL stainless steel autoclave reactor equipped with an induction stirring was purged with purified nitrogen, and purified toluene (617 mL) and methyl acrylate (72 mL, adjusted to have a concentration of 1 mol/L at the polymerization) were introduced into the autoclave in a purified nitrogen atmosphere. The catalyst solution prepared above was added thereto, and polymerization was started at room temperature under an ethylene pressure of 3 MPa. The temperature was kept at 80° C. during the reaction, and ethylene was continuously supplied to maintain the partial pressure of ethylene at 3 MPa.

After the polymerization, the ethylene was purged, and the autoclave was cooled to room temperature. In the case where the obtained polymer was a toluene-insoluble solid, the polymer and the solvent were separated by filtration. When the separation by filtration was insufficient, the polymer was reprecipitated using ethanol (1 L), and the precipitated polymer was filtered. Furthermore, the obtained solid polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby the polymer was finally recovered. The results of each polymerization are shown in Table 2.

TABLE 2

| RUN | Complex | Ligand | Activity g/mol/hr | $M_w$ X10$^3$ | $M_w/M_n$ | Tm ° C. | Comonomer Content[a] Mol % | MFR, MI (2 Kg) | MFR, MI (10 Kg) |
|---|---|---|---|---|---|---|---|---|---|
| Example 1-1 | — | (I) | 8.6E+05 | 153 | 2.4 | 118.9 | 0.9 | 0.15 | 1.11 |
| Example 1-2 | — | (II) | 3.5E+06 | 94 | 1.9 | 123.6 | 0.8 | 1.00 | 8.34 |
| Example 1-3 | — | (III) | 9.0E+05 | 160 | 1.9 | 120.6 | 1.0 | 0.11 | 0.98 |
| Example 1-4 | — | (IV) | 1.8E+06 | 168 | 2.1 | 120.4 | 1.0 | 0.16 | 1.10 |
| Example 1-5 | — | (V) | 1.7E+03 | 54 | 2.0 | 117.5 | 1.4 | 14.86 | — |
| Example 1-6 | — | (VII) | 1.1E+06 | 118 | 2.2 | 117.7 | 0.8 | 0.69 | 4.07 |
| Example 1-7 | — | (VIII) | 2.9E+06 | 143 | 2.1 | 123.8 | 0.4 | 0.32 | 1.85 |
| Example 1-8 | — | (IX) | 1.2E+06 | 119 | 2.0 | 120.2 | 1.3 | 0.77 | 5.11 |
| Example 1-9 | — | (X) | 1.4E+06 | 66 | 1.9 | 115.7 | 1.3 | 7.03 | 35.56 |
| Example 1-10 | — | (XI) | 2.6E+06 | 40 | 2.0 | 113.3 | 1.6 | 51.00 | High |
| Example 1-11 | (XII) | — | 1.4E+04 | 36 | 6.7 | 119.7 | 1.0 | — | — |
| Comparative Example 1-1 | — | (XIII) | 4.2E+05 | 14 | 2.0 | 104.2 | 2.9 | High | — |
| Comparative Example 1-2 | — | (XIV) | 6.2E+05 | 199 | 2.2 | 128.9 | 0.1 | 0.05 | 0.42 |

Conditions: Pd(dba)2/Ligand = 1; Catalyst, 100 μmol; Ethylene Pressure, 3 Mpa; MA, 1M; Toluene; 80° C.

[a]Estimated by IR.

(2) [Example 2-1]

In a 30 ml-volume flask thoroughly purged with nitrogen, 100 micromol of Nickel Complex (VII) was added and after adding dehydrated toluene (10 mL), treated by an ultrasonic vibrator for 10 minutes to prepare a catalyst slurry. Subsequently, a 1000 mL stainless steel autoclave reactor equipped with an induction stirring was purged with purified nitrogen, and purifiedtoluene (617 mL) and methyl acrylate (72 mL, adjusted to have a concentration of 1 mol/L at the polymerization) were introduced into the autoclave in a purified nitrogen atmosphere. The catalyst solution prepared above was added thereto, and polymerization was started at room temperature under an ethylene pressure of 3 MPa. The temperature was kept at room temperature during the reaction, and ethylene was continuously supplied so that the partial pressure of ethylene could be kept at 3 MPa. After 15 minutes, the ethylene was purged, and the resulting solution was concentrated by an evaporator. Thereto, 1 N-hydrochloric acid (20 ml) was added and after stirring for 60 minutes, and the polymer was filtered. The obtained solid polymer was washed with ethanol and dried under reduced pressure at 60° C. for 3 hours, whereby the product was recovered. 0.3 g, Mw: 36,000, Mw/Mn: 6.72, Tm: 120.1° C.

(3) [Comparative Example 2-1]

In a 30 ml-volume flask thoroughly purged with nitrogen, 1,000 micromol of (biscyclooctadiene)nickel and Phosphorus-Sulfonic Acid Ligand (VIII) were added and after adding dehydrated toluene (10 mL), the mixture was treated by an ultrasonic vibrator for 10 minutes to prepare a catalyst slurry. Subsequently, a 1000 mL stainless steel autoclave reactor equipped with an induction stirring was purged with purified nitrogen, and purified toluene (708 mL) and methyl acrylate (1 mol/L) were introduced into the autoclave in a purified nitrogen atmosphere. The catalyst slurry was added thereto, and polymerization was started at room temperature under an ethylene pressure of 3 MPa. The temperature was kept at room temperature during the reaction, and ethylene was continuously supplied to keep the partial pressure of ethylene at 3 MPa. After 15 minutes, the ethylene was purged, and the resulting solution was concentrated by an evaporator. Thereto, 1 N-hydrochloric acid (20 ml) was added, and the mixture was stirred for 60 minutes, but no polymer was obtained.

(4) [Examples 3-1 to 3-10 and 4-1 to 4-14 and Comparative Examples 3-1 to 3-4]

A bis(benzylideneacetone)palladium slurry and a phosphorus-sulfonic acid ligand slurry were separately prepared and mixed with an ultrasonic vibrator, and the mixture was stirred at room temperature for 15 minutes to prepare a catalyst slurry at the concentration from 0.0025 to 0.02 mol/L. Subsequently, to a 10 mL stainless steel-autoclave reactor equipped with an induction stirring and purged with purified nitrogen, purified toluene and a predetermined amount of comonomer were introduced. After raising the temperature and pressurizing the system with ethylene to 2 MPa, a predetermined amount of the catalyst slurry prepared above was added, and polymerization was started. Here, the total liquid amount was adjusted to become 5 mL during the polymerization. The temperature was kept constant during the reaction, and ethylene was continuously supplied to keep the partial pressure of ethylene at 2 MPa. After 60 minutes, the unreacted ethylene was purged, and the autoclave was cooled to room temperature. The obtained polymer was recovered by filtration and dried under reduced pressure at 40° C. for 6 hours. Detailed polymerization conditions and results are shown in Tables 3 and 4.

TABLE 3

| | Metal | | Ligand | | Yield | Activity | Mw | Mw/Mn | Tm | Comonomer Content[a] |
|---|---|---|---|---|---|---|---|---|---|---|
| | | μmol | | μmol | g | g/mol/hr | ×10³ | — | ° C. | Mol % |
| Example 3-1 | Pd(dba)2 | 2 | (I) | 2 | 0.362 | 1.8E+05 | 94 | 1.7 | 117.8 | 1.5 |
| Example 3-2 | Pd(dba)2 | 1 | (I) | 0.5 | 0.399 | 8.0E+05 | 145 | 1.6 | 117.5 | 2.2 |
| Example 3-3 | Pd(dba)2 | 4 | (II) | 2 | 0.636 | 3.2E+05 | 65 | 1.4 | 120.1 | 2.4 |
| Example 3-4 | Pd(dba)2 | 4 | (III) | 2 | 0.455 | 2.3E+05 | 107 | 1.5 | 117.8 | 2.4 |
| Example 3-5 | Pd(dba)2 | 2 | (IV) | 1 | 0.544 | 5.4E+05 | 137 | 1.6 | 121.4 | 3.7 |
| Example 3-6 | Pd(dba)2 | 1 | (V) | 1 | 0.131 | 1.3E+05 | 56 | 1.8 | 119.5 | 1.2 |
| Example 3-7 | Pd(dba)2 | 2 | (VII) | 1 | 0.716 | 7.2E+05 | 117 | 1.4 | 125.0 | |
| Example 3-8 | Pd(dba)2 | 1 | (VIII) | 0.5 | 0.126 | 2.5E+05 | 99 | 1.4 | 123.4 | |
| Example 3-9 | Pd(dba)2 | 4 | (IX) | 2 | 0.644 | 3.2E+05 | 95 | 1.5 | 119.8 | |
| Example 3-10 | Pd(dba)2 | 2 | (X) | 1 | 0.527 | 5.3E+05 | 57 | 1.3 | 111.9 | |
| Example 3-11 | Pd(dba)2 | 2 | (XI) | 1 | 0.434 | 4.3E+05 | 53 | 1.3 | 118.3 | |
| Comparative Example 3-1 | Pd(dba)2 | 4 | (XIII) | 4 | 0.214 | 5.4E+04 | 10 | 1.6 | 99.0 | 4.4 |
| Comparative Example 3-2 | Pd(dba)2 | 4 | (XIII) | 2 | 0.093 | 4.7E+04 | NES | NES | 97.1 | NES |
| Comparative Example 3-3 | Pd(dba)2 | 4 | (XIV) | 4 | 0.100 | 2.5E+04 | 144 | 1.7 | 128.0 | 0.5 |
| Comparative Example 3-4 | Pd(dba)2 | 4 | (XIV) | 2 | 0.406 | 1.0E+05 | 118 | 1.8 | 126.2 | 0.9 |

Conditions: Ethylene Pressure, 2 Mpa; MA, 6 mmol; Toluene; 80° C.; 60 min; NES (Not Enough Sample).
[a]Estimated by IR.

TABLE 4

| | Metal | | Ligand | | Comonomer | | | Temp | Yield | Activity | Comonomer Content[a] | Mw | Mw/Mn | Tm |
|---|---|---|---|---|---|---|---|---|---|---|---|---|---|---|
| | | μmol | | μmol | | mmol | | | g | g/mol/hr | mol % | ×10³ | — | ° C. |
| Example 4-1 | Pd(dba)2 | 4 | (I) | 4 | tBA | 6 | — | 80 | 0.30 | 7.5E+04 | 1.4 | 75.5 | 1.7 | 116.5 |
| Example 4-2 | Pd(dba)2 | 16 | (I) | 16 | VA | 6 | — | 80 | 0.20 | 1.3E+04 | 0.2 | 34.0 | 1.6 | 132.5 |

TABLE 4-continued

|  | Metal |  | Ligand |  | Comonomer |  |  |  | Temp | Yield g | Activity g/mol/hr | Comonomer Content[a] mol % | Mw ×10³ | Mw/Mn | Tm °C. |
|---|---|---|---|---|---|---|---|---|---|---|---|---|---|---|---|
|  |  | μmol |  | μmol |  | mmol |  | mmol |  |  |  |  |  |  |  |
| Example 4-3 | Pd(dba)2 | 16 | (I) | 16 | AA | 6 | — | — | 80 | 0.84 | 5.3E+04 | 2.1 | 31.8 | 1.5 | 123.0 |
| Example 4-4 | Pd(dba)2 | 4 | (I) | 2 | MA | 6 | — | — | 150 | 0.14 | 6.8E+04 | 1.4 | 11.7 | 1.6 | 113.8 |
| Example 4-5 | Pd(dba)2 | 8 | (I) | 4 | MA | 56 | — | — | 80 | 0.29 | 7.3E+04 | 7.2 | 53.9 | 1.6 | 90.3 |
| Example 4-6 | Pd(dba)2 | 2 | (I) | 1 | Hexene | 6 | — | — | 80 | 0.52 | 5.2E+05 |  | 52.1 | 1.8 | 120.4 |
| Example 4-7 | Pd(dba)2 | 2 | (I) | 1 | MA | 6 | Hexene | 6 | 80 | 0.06 | 6.0E+04 | 2.1(MA), 0.9(Hexene) | 108.0 | 1.6 | 114.0 |
| Example 4-8 | Pd(dba)2 | 1 | (I) | 0.5 | LUA | 6 | — | — | 80 | 0.58 | 1.2E+06 |  | 125.4 | 1.4 | 112.1 |
| Example 4-9 | Pd(dba)2 | 16 | (I) | 8 | HEA | 6 | — | — | 80 | 1.35 | 1.7E+05 |  | 43.7 | 1.3 | 119.4 |
| Example 4-10 | Pd(dba)2 | 1 | (I) | 0.5 | EUA | 6 | — | — | 80 | 0.12 | 2.4E+05 |  | 48.3 | 1.3 | 121.3 |
| Example 4-11 | Pd(dba)2 | 4 | (I) | 2 | NBMOH | 6 | — | — | 80 | 0.73 | 3.7E+05 |  | 71.8 | 1.5 | 122.3 |
| Example 4-12 | Pd(dba)2 | 2 | (I) | 1 | NBYA | 6 | — | — | 80 | 0.60 | 6.0E+05 |  | 67.2 | 1.4 | 112.2 |
| Example 4-13 | Pd(dba)2 | 4 | (I) | 2 | ATMS | 6 | — | — | 80 | 0.25 | 1.3E+05 |  | 48.2 | 1.3 | 127.8 |
| Example 4-14 | Pd(dba)2 | 4 | (I) | 2 | BTOH | 6 | — | — | 80 | 0.14 | 3.5E+04 |  | 24.1 | 1.4 | 128.5 |

Conditions: Ethylene Pressure, 2 Mpa; Toluene; 80° C.; 60 min.
[a]Estimated by IR.

(5) [Examples 5-1 to 5-12, 6-1 to 6-4, 7-1 to 7-12 and Comparative Examples 5-1 and 5-2]

To a 10 mL stainless steel-autoclave reactor equipped with an induction stirring and purged with purified nitrogen, purified toluene and a predetermined amount of comonomer were introduced. After raising the temperature, the system was pressured with ethylene to 2 MPa. A toluene solution of (biscyclooctadiene)nickel and a toluene solution of phosphorus-sulfonic acid ligand were separately prepared and added each in a predetermined amount in the order of (biscyclooctadiene)nickel and phosphorus-sulfonic acid ligand, and the polymerization was started. In the case of using a third component such as aniline, this component was added after the addition of (biscyclooctadiene)nickel but before adding the phosphorus-sulfonic acid ligand. Here, the total liquid amount was adjusted to become 5 mL during the polymerization. The temperature was kept constant during the reaction, and ethylene was continuously supplied to keep the partial pressure of ethylene at 2 MPa. After 60 minutes, the unreacted ethylene was purged, and the autoclave was cooled to room temperature. After removing the solvent by evaporation, the residue was washed suing a small amount of acetone, and the polymer was recovered by filtration and dried under reduced pressure at 40° C. for 6 hours. The polymerization conditions and results are shown in Tables 5, 6 and 7 below.

TABLE 5

|  | Ligand |  | Comonomer |  | Yield g | Activity g/mol/hr | Mw ×10³ | Mw/Mn | Tm °C. | Comonomer Content[a] mol % |
|---|---|---|---|---|---|---|---|---|---|---|
|  |  | μmol |  | mmol |  |  |  |  |  |  |
| Example 5-1 | (I) | 16 | MA | 2 | 1.15 | 7.2E+04 | 12.8 | 1.7 | 127.4 | 0.4 |
| Example 5-2 | (I) | 16 | tBA | 2 | 0.42 | 2.6E+04 | 9.2 | 1.7 | 126.2 | 1.0 |
| Example 5-3 | (I) | 8 | tBA | 0.5 | 0.63 | 7.9E+04 | 27.2 | 1.5 | 130.5 | 0.3 |
| Example 5-4 | (III) | 16 | MA | 2 | 0.04 | 2.4E+03 | NES | NES | 123.8 | 2.1 |
| Example 5-5 | (III) | 16 | tBA | 2 | 0.35 | 2.2E+04 | 8.6 | 1.9 | 126.1 | 1.1 |
| Example 5-6 | (III) | 16 | EA | 2 | 0.07 | 4.4E+03 | 6.1 | 1.6 | 124.5 | 1.4 |
| Example 5-7 | (III) | 16 | AA | 2 | 0.02 | 1.3E+03 | NES | NES | NES | NES |
| Example 5-8 | (III) | 8 | tBA | 0.5 | 0.63 | 7.9E+04 | 26.4 | 1.4 | 130.2 | 0.3 |
| Example 5-9 | (IV) | 8 | tBA | 0.5 | 0.32 | 4.0E+04 | 25.5 | 1.6 | 129.8 | 0.5 |
| Example 5-10 | (VI) | 16 | tBA | 2 | 0.02 | 1.0E+03 | 21.8 | 2.4 | 121.5 | NES |
| Example 5-11 | (VII) | 16 | tBA | 0.5 | 0.71 | 4.5E+04 | 15.2 | 1.5 | 128.7 | 0.6 |
| Example 5-12 | (VIII) | 16 | tBA | 0.5 | 1.24 | 7.8E+04 | 22.3 | 1.7 | 128.4 | 0.3 |
| Comparative Example 5-1 | (XIII) | 16 | tBA | 0.5 | 0.07 | 4.1E+03 | NES | NES | NES | NES |
| Comparative Example 5-2 | (XIV) | 8 | tBA | 0.5 | 0.51 | 6.4E+04 | 9.5 | 1.5 | 112.2 | 0.1 |

Conditions: Ni(cod)2/Ligand = 1; Ethylene Pressure, 2 Mpa; Toluene; 40° C.; 60 min; NES (Not Enough Sample).
[a]Estimated by IR.

TABLE 6

|  | Complex |  | Ligand |  | Comonomer |  | Temp °C. | 3rd Component |  | Yield g | Activity g/mol/hr | Mw ×10³ | Mw/Mn | Tm °C. | Comonomer Content[a] mol % |
|---|---|---|---|---|---|---|---|---|---|---|---|---|---|---|---|
|  |  | μmol |  | μmol |  | mmol |  |  | mmol |  |  |  |  |  |  |
| Example 6-1 | — | — | (I) | 16 | MA | 2 | 60 | Aniline | 8 | 0.087 | 5.4E+03 | 4.9 | 1.7 | 125.2 | 1.2 |
| Example 6-2 | — | — | (III) | 16 | MA | 2 | 60 | MMA | 8 | 0.041 | 2.6E+03 | 6.4 | 1.8 | 124.9 | 2.2 |

TABLE 6-continued

| | Complex | | Ligand | | Comonomer | Temp | 3rd Component | | Yield | Activity | Mw | Mw/Mn | Tm | Comonomer Content[a] |
|---|---|---|---|---|---|---|---|---|---|---|---|---|---|---|
| | | μmol | | μmol | mmol | °C. | | mmol | g | g/mol/hr | ×10³ | — | °C. | mol % |
| Example 6-3 | — | — | (III) | 16 | MA 2 | 60 | clay | 10 mg | 0.054 | 3.4E+03 | 5.9 | 1.7 | 124.6 | — |
| Example 6-4 | (XI) | 8 | — | — | tBA 2 | 40 | TPB | 1 | 0.057 | 7.1E+03 | NES | NES | 114.7 | 0.9 |

Conditions: Ni(cod)2/Ligand = 1; Ethylene Pressure, 2 Mpa; Toluene; 60 min; NES (Not Enough Sample).
[a]Estimated by IR.

TABLE 7

| | Complex | | Ligand | | Temp | Yield | Activity | Mw | Mw/Mn | Tm |
|---|---|---|---|---|---|---|---|---|---|---|
| | | μmol | | μmol | °C. | g | g/mol/hr | ×10³ | — | °C. |
| Example 7-1 | — | — | (I) | 4 | 60 | 1.21 | 3.0E+05 | 22.3 | 2.0 | 125.6 |
| Example 7-2 | — | — | (I) | 8 | 40 | 1.06 | 1.3E+05 | 45.1 | 1.9 | 123.9 |
| Example 7-3 | — | — | (III) | 2 | 40 | 0.76 | 3.8E+05 | 47.6 | 1.6 | 127.5 |
| Example 7-4 | — | — | (IV) | 4 | 40 | 1.15 | 2.9E+05 | 27.2 | 1.7 | 125.2 |
| Example 7-5 | — | — | (V) | 4 | 60 | 0.32 | 7.9E+04 | 2.0 | 1.5 | 104.4 |
| Example 7-6 | — | — | (VI) | 4 | 60 | 0.94 | 2.4E+05 | 5.2 | 2.1 | 126.6 |
| Example 7-7 | — | — | (VII) | 4 | 40 | 0.95 | 2.4E+05 | 33.9 | 1.7 | 127.9 |
| Example 7-8 | — | — | (VIII) | 4 | 40 | 1.53 | 3.8E+05 | 15.9 | 1.8 | 120.5 |
| Example 7-9 | — | — | (IX) | 2 | 40 | 1.32 | 6.6E+05 | 51.4 | 1.7 | 130.4 |
| Example 7-10 | — | — | (X) | 4 | 40 | 1.25 | 3.1E+05 | 8.9 | 1.4 | 119.6 |
| Example 7-11 | — | — | (XI) | 4 | 40 | 1.00 | 2.5E+05 | 33.4 | 1.8 | 122.4 |
| Example 7-12 | (XII) | 2 | — | — | 40 | 0.58 | 2.9E+05 | 4.0 | 1.3 | 110.1 |

Conditions: Ni(cod)2/Ligand = 1; Ethylene Pressure, 2 Mpa; Toluene; 60 min.

(6) [Examples 8-1, 8-2, 9-1 and 9-2]

A methylene chloride solution or slurry of (bisbenzylideneacetone)palladium and a methylene chloride solution or slurry of phosphorus-sulfonic acid ligand were separately prepared and mixed at room temperature, and the mixture was by an ultrasonic vibrator for 30 minutes to prepare a catalyst slurry at the concentration from 0.0025 to 0.02 mol/L. Thereafter, a predetermined amount of a methylene chloride slurry (40 mg-clay/ml-toluene) of the chemically treated montmorillonite, which was obtained in Treatment Example 1 or Treatment Example 2, was added to the catalyst slurry and further stirred at room temperature for 30 minutes to obtain a supported catalyst slurry. The polymerization evaluation was performed for a case where the supported catalyst slurry obtained here was directly used in the polymerization evaluation and for a case where the slurry was washed with methylene chloride to a residual liquid ratio of 1/100 and then used.

The 10 mL stainless steel-autoclave reactor equipped with an induction stirring was purged with purified nitrogen, and purified toluene and a predetermined amount of comonomer were introduced. After raising the temperature and then pressurizing the system with ethylene to 2 MPa, a predetermined amount of the supported catalyst slurry prepared above was added, and polymerization was started. Here, the total liquid amount was adjusted to become 5 mL during the polymerization. The temperature was kept at 80° C. during the reaction, and ethylene was continuously supplied to keep the partial pressure of ethylene at 2 MPa. After 60 minutes, the unreacted ethylene was purged, and the autoclave was cooled to room temperature. The obtained polymer was recovered by filtration and dried under reduced pressure at 40° C. for 6 hours. Detailed polymerization conditions and results are shown in Table 8.

(7) [Examples 10-1 to 10-3, 11-1 and 11-2 and Comparative Examples 11-1 and 11-2]

A toluene solution or slurry of (biscyclooctadiene)nickel and a toluene solution or slurry of phosphorus-sulfonic acid ligand were separately prepared and mixed using an ultrasonic vibrator for 30 minutes at room temperature to prepare a catalyst slurry at the concentration from 0.0025 to 0.02 mol/L. Thereafter, a predetermined amount of a toluene slurry (40 mg-clay/ml-toluene) of the chemically treated clay, which was obtained in Treatment Example 1 or Treatment Example 2 of Chemically Treated Montmorillonite was added to the catalyst slurry and further stirred at room temperature for 30 minutes to obtain a supported catalyst slurry. The polymerization evaluation was performed for a case where the supported catalyst slurry obtained here was directly used in the polymerization evaluation and for a case where the slurry was washed with toluene to a residual liquid ratio of 1/100 and then used.

The 10 mL stainless steel-autoclave reactor equipped with an induction stirring was purged with purified nitrogen, purified toluene and a predetermined amount of comonomer were introduced. After raising the temperature and then pressurizing the system with ethylene to 2 MPa, a predetermined amount of the supported catalyst slurry prepared above was added, and polymerization was started. Here, the total liquid amount was adjusted to become 5 mL during the polymerization. The temperature was kept at 80° C. during the reaction, and ethylene was continuously supplied to keep the partial pressure of ethylene at 2 MPa. After 60 minutes, the unreacted ethylene was purged, and the autoclave was cooled to room temperature. The obtained polymer was recovered by filtration and dried under reduced pressure at 40° C. for 6 hours. Detailed polymerization conditions and results are shown in Table 9.

TABLE 8

| | Ligand | | Clay Treatment | | Washing of Catalyst | Comonomer | | Yield | Activity | Comonomer Content[a] | Mw | Mw/Mn | Tm |
|---|---|---|---|---|---|---|---|---|---|---|---|---|---|
| | | μmol | Example | mg | Component | | mmol | g | g/mol/hr | mol % | ×10³ | — | ° C. |
| Example 8-1 | (I) | 2 | (1) | 10 | none | — | — | 0.80 | 4.0E+05 | — | 106.9 | 1.5 | 132.1 |
| Example 8-2 | (I) | 2 | (1) | 10 | none | MA | 6 | 0.23 | 1.1E+05 | 1.9 | 126.1 | 1.4 | 113.3 |
| Example 9-1 | (I) | 2 | (2) | 10 | none | — | — | 0.46 | 2.3E+05 | — | 96.0 | 1.4 | 132.2 |
| Example 9-2 | (I) | 2 | (2) | 10 | none | | 6 | 0.20 | 1.0E+05 | 2.0 | 110.4 | 1.4 | 118.9 |

Conditions: Pd(dba)2/Ligand = 1; Ethylene Pressure, 2 MPa; Time, 60 min; Toluene; 80° C.;
[a]Estimated by IR.

TABLE 9

| | Ligand | | Clay Treatment | | Washing of Catalyst | Comonomer | | Yield | Activity | Comonomer Content[a] | Mw | Mw/Mn |
|---|---|---|---|---|---|---|---|---|---|---|---|---|
| | | μmol | Example | mg | Component | | mmol | g | g/mol/hr | mol % | ×10³ | — |
| Example 10-1 | (IV) | 2 | (1) | 10 | none | — | — | 1.61 | 8.0E+05 | — | 12.3 | 1.6 |
| Example 10-2 | (IV) | 4 | (1) | 20 | none | tBA | 0.5 | 0.03 | 6.8E+03 | 0.2 | 16.9 | 1.8 |
| Example 10-3 | (IV) | 2 | (1) | 10 | washed | — | — | 0.68 | 6.8E+05 | — | 15.0 | 1.5 |
| Example 11-1 | (IV) | 2 | (2) | 10 | none | — | — | 1.59 | 8.0E+05 | — | 17.9 | 1.2 |
| Example 11-2 | (IV) | 4 | (2) | 20 | none | tBA | 0.5 | 0.05 | 1.2E+04 | NES | 12.0 | 1.6 |
| Example 11-3 | (IV) | 2 | (2) | 10 | washed | — | — | 0.93 | 4.6E+05 | — | 15.4 | 1.5 |
| Comparative Example 11-1 | (XII) | 2 | (2) | 10 | none | — | — | 0.03 | 1.3E+04 | — | NES | NES |
| Comparative Example 11-2 | (XII) | 2 | (2) | 10 | washed | — | — | 0.01 | 6.0E+03 | — | NES | NES |

Conditions: Ni(cod)2/Ligand = 1; Ethylene Pressure, 2 MPa; Time, 60 min; Toluene; 80° C.; NES (not Enough Sample).
[a]Estimated by IR.

(8) [Example 12: copolymerization of ethylene/1-hexene/ethyl acrylate]

In a 30 ml-volume flask thoroughly purged with nitrogen, 200 micromol of bis(benzylideneacetone)palladium and Phosphorus-Sulfonic Acid Ligand (I) were weighed and dehydrated toluene (10 mL) was added. The mixture was treated by an ultrasonic vibrator for 10 minutes to prepare a catalyst slurry. Subsequently, To a 1000 mL stainless steel autoclave reactor equipped with an induction stirring and purged with purified nitrogen, toluene (170 mL), 1-hexene (279 mL) and ethyl acrylate (245 mL) were introduced in a purified nitrogen atmosphere. The entire amount of the catalyst slurry prepared above was added thereto, and polymerization was started by pressurizing the system with ethylene to 3 MPa. The temperature was kept at 80° C. during the reaction, and ethylene was continuously supplied to maintain the pressure of ethylene at 3 MPa. After 180 minutes, the ethylene was purged, and the autoclave was cooled to room temperature. The polymer was reprecipitated using ethanol (1 L) and the precipitated polymer was filtered. Furthermore, the obtained solid polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby the polymer was finally recovered.

Here, 74 g of an ethylene/1-hexene/ethyl acrylate copolymer was obtained. The catalytic activity was 1.2E+05 g/mol/h, Mw by GPC was 92,000, Mw/Mn was 2.1, the melting point was 102.9° C., and the monomer incorporation was an ethylene content of 96.3 mol %, a 1-hexene content of 1.1 mol %, and an ethyl acrylate content of 2.6 mol % (13C NMR). The polymerization conditions and results are shown in Tables 10 and 11.

(9) [Examples 13 to 22: copolymerization of ethylene/1-hexene/ethyl acrylate]

In a 30 ml-volume flask thoroughly purged with nitrogen, palladium bisbenzylideneacetone and Phosphorus-Sulfonic Acid Ligand (I) were weighed each in the predetermined amount shown in Table 10 and after adding dehydrated toluene (10 mL), the mixture was treated by an ultrasonic vibrator for 10 minutes to prepare a catalyst slurry. Subsequently, the inside of an induction stirring-type stainless steel-made autoclave having an inner volume of 2.4 liter was purged with purified nitrogen, and purified toluene (in Example 22, hexane was used in place of toluene), ethyl acrylate and 1-hexene each in the predetermined amount shown in Table 10 were introduced into the autoclave.

The inside of the autoclave was controlled to a predetermined amount and the pressure in the autoclave was raised to 0.1 MPa by nitrogen. Furthermore, the ethylene partial pressure was raised (total pressure=ethylene partial pressure+0.1).

After the temperature in the autoclave was stabilized, the catalyst slurry prepared above was pressed into the autoclave by a small amount of nitrogen to start polymerization. The temperature was kept at a predetermined temperature during the reaction, and ethylene was continuously supplied so that the pressure could be kept at a predetermined pressure.

After the polymerization for a predetermined time, the ethylene was purged, and the autoclave was cooled to room temperature, thereby stopping the polymerization. The produced polymer was washed by adding the reaction solution to 1 L of acetone and separated by filtration. The separated polymer was subjected to acetone washing and filtration and after repeating this operation twice, dried under reduced pressure at 60° C. for 3 hours, whereby the polymer was finally recovered. The results of each polymerization are shown in Table 11.

TABLE 10

| | Cat. | Solvent | | EA | | 1-Hexene | | Ethylene Press. | Temp. | Time |
|---|---|---|---|---|---|---|---|---|---|---|
| | μmol | | ml | ml | mol/l | ml | mol/l | MPa | °C. | min |
| Example 12 | 200 | Toluene | 170 | 245 | 3.2 | 279 | 3.2 | 3.0 | 80 | 180 |
| Example 13 | 100 | Toluene | 640 | 110 | 1.0 | 250 | 2.0 | 2.0 | 80 | 90 |
| Example 14 | 300 | Toluene | 300 | 500 | 5.1 | 100 | 0.9 | 2.0 | 80 | 240 |
| Example 15 | 200 | Toluene | 260 | 390 | 4.0 | 250 | 2.2 | 2.0 | 80 | 240 |
| Example 16 | 200 | Toluene | 540 | 110 | 1.1 | 250 | 2.2 | 2.0 | 70 | 60 |
| Example 17 | 200 | Toluene | 690 | 60 | 0.6 | 150 | 1.3 | 1.5 | 90 | 60 |
| Example 18 | 100 | Toluene | 540 | 60 | 0.6 | 300 | 2.7 | 1.5 | 90 | 60 |
| Example 19 | 100 | Toluene | 500 | 60 | 0.6 | 340 | 3.0 | 2.0 | 90 | 60 |
| Example 20 | 200 | Toluene | 150 | 350 | 3.6 | 400 | 3.5 | 3.0 | 60 | 240 |
| Example 21 | 200 | Toluene | 100 | 300 | 3.1 | 500 | 4.4 | 2.0 | 60 | 240 |
| Example 22 | 200 | n-Hexane | 100 | 300 | 3.1 | 500 | 4.4 | 2.0 | 60 | 240 |

Conditions: Pd(dba)2/(Ligand (I)) = 1

TABLE 11

| RUN | Yield g | Activity g/mol/h | MFR g/10 min | FR — | Mw $10^{-4}$ | Mw/Mn — | d g/cm$^3$ | Tm °C. | EA Content mol %$^a$ | 1-Hexene Content mol %$^a$ |
|---|---|---|---|---|---|---|---|---|---|---|
| Example 12 | 74 | 1.2E+05 | 1.9 | 6.4 | 9.2 | 2.1 | 0.9328 | 102.9 | 2.6 | 1.1 |
| Example 13 | 38 | 2.6E+05 | 0.8 | 5.3 | 12.5 | 1.8 | 0.9246 | 111.2 | 1.2 | 0.9 |
| Example 14 | 49 | 4.1E+04 | 3.2 | 5.3 | 8.6 | 2.0 | 0.9344 | 95.7 | 4.5 | 0.4 |
| Example 15 | 37 | 4.7E+04 | 3.8 | 5.3 | 8.4 | 2.0 | 0.9307 | 96.0 | 3.8 | 0.9 |
| Example 16 | 60 | 3.0E+05 | 0.5 | 5.8 | 14.2 | 1.9 | 0.9257 | 112.4 | 1.1 | 0.8 |
| Example 17 | 78 | 3.9E+05 | 5.2 | 5.7 | 7.3 | 1.8 | 0.9267 | 110.0 | 1.0 | 1.4 |
| Example 18 | 45 | 4.5E+05 | 8.7 | 5.3 | 7.2 | 1.8 | 0.9228 | 106.1 | 1.0 | 1.9 |
| Example 19 | 47 | 4.7E+05 | 5.6 | 5.3 | 7.6 | 1.9 | 0.9221 | 110.7 | 0.6 | 1.8 |
| Example 20 | 42 | 5.3E+04 | 0.1 | 19.2 | 16.5 | 3.0 | 0.9287 | 117.6 | 0.8 | 0.5 |
| Example 21 | 31 | 3.9E+04 | 0.8 | 6.8 | 12.1 | 2.1 | 0.9250 | 105.2 | 2.0 | 1.2 |
| Example 22 | 23 | 2.9E+04 | 1.1 | 6.4 | 11.1 | 2.0 | 0.9244 | 104.5 | 2.3 | 1.1 |

$^a$Estimated by $^{13}$C NMR

(10) [Example 23: copolymerization of ethylene/propylene/methyl acrylate]

In a 30 ml-volume flask thoroughly purged with nitrogen, palladium bisbenzylideneacetone and Phosphorus-Sulfonic Acid Ligand (I) were weighed each in an amount of 100 micromol and after adding dehydrated toluene (10 mL), the mixture was treated by an ultrasonic vibrator for 10 minutes to prepare a catalyst slurry. Subsequently, a 1000 mL stainless steel autoclave reactor equipped with an induction stirring was purged with purified nitrogen, and purified toluene (617 mL) and methyl acrylate (72 mL, adjusted to have a concentration of 1 mol/L at the polymerization) were introduced into the autoclave in a purified nitrogen atmosphere. The entire amount of the catalyst slurry prepared above was added thereto, and polymerization was started by pressurizing the system to a pressure of 1.0 MPa with an ethylene/propylene mixed gas (gas compositional ratio: 7/3) previously adjusted to 80° C. by using a separate autoclave. The temperature was kept at 80° C. during the reaction, and the mixed gas was continuously supplied so that the pressure could be kept at 1.0 MPa. After 60 minutes, the mixed gas was purged, and the autoclave was cooled to room temperature. The polymer was reprecipitated using ethanol (1 L), and the precipitated polymer was filtered. Furthermore, the obtained solid polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby 7.0 g of an ethylene/propylene/ethyl acrylate copolymer was finally recovered. The catalytic activity was 6.6E+04 g/mol/h. The molecular weight Mw of the obtained copolymer was 65,000, Mw/Mn was 1.9, the melting point was 92.1° C., the methyl acrylate content was 3.7 mol %, and the propylene content was 2.4 mol %. The polymerization results are shown in Table 12.

(11) [Example 24: copolymerization of ethylene/propylene/methyl acrylate]

In a 30 ml-volume flask thoroughly purged with nitrogen, palladium bisbenzylideneacetone and Phosphorus-Sulfonic Acid Ligand (I) were weighed each in an amount of 264 micromol and after adding dehydrated toluene (20 mL), the mixture was treated by an ultrasonic vibrator for 10 minutes to prepare a catalyst slurry.

A separate 2 L-volume induction stirring-type autoclave was previously prepared as a buffer tank for an ethylene/propylene mixed gas. Liquefied propylene (150 mL) and ethylene (2.5 MPa) were charged into this tank at 20° C. and stirred until these were thoroughly mixed and then, the temperature was raised to 50° C.

Subsequently, the inside of an induction stirring-type stainless steel-made autoclave having an inner volume of 2 liters for use in the polymerization was purged with purified nitrogen, and purified toluene (500 mL), methyl acrylate (37.5 mL) and the entire amount of the catalyst slurry prepared above were introduced into the autoclave in a purified nitrogen atmosphere. Propylene (100 mL) was introduced into the autoclave at 20° C., and the mixed gas prepared above was introduced to raise the pressure to 1.2 MPa. Thereafter, the temperature was raised to 70° C., and the mixed gas was added so that the total pressure could become 2.0 MPa. The mixed gas was appropriately introduced to keep the total pressure during the polymerization. After 10 minutes, ethanol (25 ml) was charged, and the unreacted gas was purged, thereby stopping the polymerization. The recovered toluene suspension was added with ethanol (1,000 mL), and the mixture was left standing still for one night and then filtered. Acetone (500 ml) was added to the precipitate and after stirring at 20° C. for 20 minutes, filtration was performed. This washing was performed two more times. After the washing, the polymer was dried under reduced pressure at 70° C. for 3 hours to obtain 23.2 g of an ethylene-propylene-methyl acrylate copolymer (catalytic activity: 5.3E+05 (g/mol/h)). The melting point by DSC of the obtained copolymer was 107.2° C., Mw by GPC was 80,000, Mw/Mn was 1.7, the methyl acrylate content was 1.0 mol %, and the propylene content was 3.0 mol %. The polymerization results are shown in Table 12.

(12) [Example 25copolymerization of ethylene/propylene/methyl acrylate]

In a 100 ml-volume flask thoroughly purged with nitrogen, palladium bisbenzylideneacetone and Phosphorus-Sulfonic Acid Ligand (I) were weighed each in an amount of 580 micromol and after adding dehydrated toluene (50 mL), the mixture was treated by an ultrasonic vibrator for 10 minutes to prepare a catalyst slurry.

A separate 2 L-volume induction stirring-type autoclave was previously prepared as a buffer tank for an ethylene/propylene mixed gas. Liquefied propylene (150 mL) and ethylene (2.5 MPa) were charged into this tank at 20° C. and stirred until these were thoroughly mixed and then, the temperature was raised to 50° C.

Subsequently, the inside of an induction stirring-type stainless steel-made autoclave having an inner volume of 2 liters for use in the polymerization was purged with purified nitrogen, and purified toluene (500 mL), methyl acrylate (37.5 mL) and the entire amount of the catalyst slurry prepared above were introduced into the autoclave in a purified nitrogen atmosphere. Propylene (100 mL) was introduced into the autoclave at 20° C., and the mixed gas prepared above was introduced to raise the pressure to 1.2 MPa. Thereafter, the temperature was raised to 55° C., and the mixed gas was added so that the total pressure could become 2.0 MPa. The mixed gas was appropriately introduced to keep the total pressure during the polymerization. After 25 minutes, ethanol (25 ml) was charged, and the unreacted gas was purged, thereby stopping the polymerization. The recovered toluene suspension was added with ethanol (1,000 mL), and the mixture was left standing still for one night and then filtered. Acetone (500 mL) was added to the precipitate and after stirring at 20° C. for 20 minutes, filtration was performed. This washing was performed two more times. After the washing, the polymer was dried under reduced pressure at 70° C. for 3 hours to obtain 19.6 g of an ethylene-propylene-methyl acrylate copolymer (catalytic activity: 8.1E+04 (g/mol/h)). The melting point by DSC of the obtained copolymer was 113.6° C., Mw by GPC was 58,000, Mw/Mn was 1.6, the methyl acrylate content was 0.6 mol %, and the propylene content was 2.4 mol %. The polymerization results are shown in Table 12.

(13) [Example 26: copolymerization of ethylene/propylene/methyl acrylate]

In a 50 ml-volume flask thoroughly purged with nitrogen, palladium bisbenzylideneacetone and Phosphorus-Sulfonic Acid Ligand (I) were weighed each in an amount of 256 micromol and after adding dehydrated toluene (20 mL), the mixture was treated by an ultrasonic vibrator for 10 minutes to prepare a catalyst slurry.

A separate 2 L-volume induction stirring-type autoclave was previously prepared as a buffer tank for an ethylene/propylene mixed gas. Liquefied propylene (150 mL) and ethylene (2.5 MPa) were charged into this tank at 20° C. and stirred until these were thoroughly mixed and then, the temperature was raised to 50° C.

Subsequently, the inside of an induction stirring-type stainless steel-made autoclave having an inner volume of 2 liters for use in the polymerization was purged with purified nitrogen, and purified toluene (500 mL), methyl acrylate (46.9 mL) and the entire amount of the catalyst slurry prepared above were introduced into the autoclave in a purified nitrogen atmosphere. Propylene (100 mL) was introduced into the autoclave at 20° C., and the mixed gas prepared above was introduced to raise the pressure to 1.2 MPa. Thereafter, the temperature was raised to 55° C., and the mixed gas was added so that the total pressure could become 2.0 MPa. The mixed gas was appropriately introduced to keep the total pressure during the polymerization. After 30 minutes, ethanol (25 ml) was charged, and the unreacted gas was purged, thereby stopping the polymerization. The recovered toluene suspension was added with ethanol (1,000 mL), and the mixture was left standing still for one night and then filtered. The obtained precipitate was added with toluene (100 mL) and 35% hydrochloric acid (0.5 mL), and the mixture was stirred at 70° C. for 30 minutes and again filtered. Acetone (500 mL) was added to the precipitate and after stirring at 20° C. for 20 minutes, filtration was performed. This washing was performed two more times. After the washing, the polymer was dried under reduced pressure at 70° C. for 3 hours to obtain 1.87 g of an ethylene-propylene-methyl acrylate copolymer (catalytic activity: 1.5E+04 (g/mol/h)). The melting point by DSC of the obtained copolymer was 120.1° C., Mw by GPC was 55,000, Mw/Mn was 1.9, the methyl acrylate content was 0.6 mol %, and the propylene content was 1.0 mol %. The polymerization results are shown in Table 12.

TABLE 12

| RUN | Yield g | Activity g/mol/h | MFR g/10 min | Mw $10^{-4}$ | Mw/Mn — | Tm ° C. | MA Content mol %[a] | Propylene Content mol %[a] |
|---|---|---|---|---|---|---|---|---|
| Example 23 | 7.0 | 6.6E+04 | 1.9 | 6.5 | 1.9 | 92.1 | 3.7 | 2.4 |
| Example 24 | 23.2 | 5.3E+05 | — | 8.0 | 1.7 | 107.2 | 1.0 | 3.0 |
| Example 25 | 19.6 | 8.1E+04 | — | 5.8 | 1.6 | 113.6 | 0.6 | 2.4 |
| Example 26 | 1.87 | 1.5E+04 | — | 5.5 | 1.9 | 120.1 | 0.6 | 1.0 |

[a]Estimated by $^{13}$C NMR

(14) [Examples 27 to 29: ethylene homopolymerization]

In a 30 ml-volume flask thoroughly purged with nitrogen, palladium bisbenzylideneacetone and phosphorus-sulfonic acid ligand (I) were weighed each in an amount of 25 micromol by using the phosphorus-sulfonic acid ligand shown in Table 13 and after adding dehydrated toluene (10 mL), the mixture was treated by an ultrasonic vibrator for 10 minutes to prepare a catalyst slurry. Subsequently, a 1000 mL stainless steel autoclave reactor equipped with an induction stirring was purged with purified nitrogen, and purified toluene (790 mL) was introduced into the autoclave in a purified nitrogen atmosphere. The entire amount of the catalyst slurry prepared above was added and after raising the temperature to 80° C., the system was pressurized at an ethylene pressure of 3.0 MPa to start the polymerization. The temperature was kept at 80° C. during the reaction, and the mixed gas was continuously supplied so that the partial pressure could be kept at 3.0 MPa. After 60 minutes, the ethylene gas was purged, and the autoclave was cooled to room temperature. The precipitated polymer was filtered. Furthermore, the obtained polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby an ethylene homopolymer was finally recovered. The polymerization results are shown in Table 13.

The polyethylene homopolymer of Example 27 was measured by 13C-NMR, as a result, a short-chain branch such as methyl ethyl was unrecognized and was below the detection limit, and the homopolymer was confirmed to be a polyethylene with a very small amount of short-chain branches.

induction stirring was purged with purified nitrogen, and purified toluene and methyl acrylate each in the predetermined amount shown in Table 14 were introduced into the autoclave in a purified nitrogen atmosphere. The catalyst solution prepared above was added thereto, and polymerization was started at room temperature under an ethylene pressure of 3 MPa. The temperature was kept at 80° C. during the reaction, and ethylene was continuously supplied for a predetermined time so that the partial pressure of ethylene could be kept at 3 MPa.

After the completion of polymerization, the ethylene was purged, and the autoclave was cooled to room temperature. In the case where the obtained polymer was a toluene-insoluble solid, the polymer and the solvent were separated by filtration. When the separation by filtration was insufficient, the polymer was reprecipitated using ethanol (1 L), and the precipitated polymer was filtered. Furthermore, the obtained solid polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby the polymer was finally recovered. The results of each polymerization are shown in Table 14.

As a result of confirmation by 13C-NMR, ethyl acrylate was inserted in the main chain, and a short-chain branch such as methyl ethyl could not be recognized.

TABLE 13

| RUN | Ligand | Yield g | Activity g/mol/h | MFR g/10 min | FR | Mw $10^{-4}$ | Mw/Mn — | Tm ° C. |
|---|---|---|---|---|---|---|---|---|
| Example 27 | (I) | 41.1 | 1.6E+06 | 1.9 | 21.1 | 17.4 | 2.4 | 135.1 |
| Example 28 | (III) | 18.7 | 7.5E+05 | 0.06 | 8.6 | 19.0 | 2.5 | 137.1 |
| Example 29 | (IV) | 29.9 | 1.8E+06 | — | — | 16.8 | 2.1 | 133.8 |

Conditions: Pd(dba)2/Ligand = 1; Catalyst, 25 μmol; Ethylene, 3 MPa; 80° C., 1 h.

(15) [Examples 30 and 31: copolymerization of ethylene-ethyl acrylate]

In a 30 ml-volume flask thoroughly purged with nitrogen, palladium bisbenzylideneacetone and Phosphorus-Sulfonic Acid Ligand (I) were weighed each in the predetermined amount shown in Table 14 and after adding dehydrated toluene (10 mL), the mixture was treated by an ultrasonic vibrator for 10 minutes to prepare a catalyst slurry. Subsequently, a 1000 mL stainless steel autoclave reactor equipped with an

TABLE 14

| RUN | Ligand μmol | Toluene mL | EA mL | EA mol/L | Time min | Yield g | Activity g/mol/h | MFR g/10 min | FR | Mw $10^{-4}$ | Mw/Mn — | d g/cm$^3$ | Tm ° C. | EA Content mol %[a] |
|---|---|---|---|---|---|---|---|---|---|---|---|---|---|---|
| Example 30 | 200 | 445 | 245 | 3.0 | 90 | 45.6 | 1.5E+05 | 0.38 | 6.91 | 13.1 | 2.1 | 0.9313 | 110.2 | 2.5 |
| Example 31 | 100 | 614 | 76 | 1.0 | 60 | 71.4 | 7.1E+05 | 0.29 | 7.60 | 13.4 | 2.1 | 0.9308 | 118.8 | 1.3 |

Conditions: Pd(dba)2/(Ligand(I)) = 1; Catalyst, 25 μmol; Ethylene Pressure, 3 MPa; 80° C.
[a]Estimated by $^{13}$C NMR.

(16) [Examples 32 and 33: copolymerization of ethylene-1-hexene]

In a 30 ml-volume flask thoroughly purged with nitrogen, palladium bisbenzylideneacetone and Phosphorus-Sulfonic Acid Ligand (I) were weighed each in the predetermined amount shown in Table 15 and after adding dehydrated toluene (10 mL), the mixture was treated by an ultrasonic vibrator for 10 minutes to prepare a catalyst slurry. Subsequently, a 1000 mL stainless steel autoclave reactor equipped with an induction stirring was purged with purified nitrogen, and purifiedtoluene and 1-hexene each in the predetermined amount shown in Table 15 were introduced into the autoclave in a purified nitrogen atmosphere. The catalyst solution prepared above was added thereto, and polymerization was started at room temperature under an ethylene pressure of 3 MPa. The temperature was kept at 80° C. during the reaction, and ethylene was continuously supplied for a predetermined time so that the partial pressure of ethylene could be kept at 3 MPa.

After the completion of polymerization, the ethylene was purged, and the autoclave was cooled to room temperature. In the case where the obtained polymer was a toluene-insoluble solid, the polymer and the solvent were separated by filtration. When the separation by filtration was insufficient, the polymer was reprecipitated using ethanol (1 L), and the precipitated polymer was filtered. Furthermore, the obtained solid polymer was dispersed in ethanol (1 L), and 1 N-hydrochloric acid (20 ml) was added thereto. This mixture was stirred for 60 minutes, and the polymer was filtered. The obtained solid polymer was washed with ethanol and dried under reduced pressure at 60° C. for 3 hours, whereby the polymer was finally recovered. The results of each polymerization are shown in Table 15.

TABLE 15

| RUN | Toluene mL | 1-Hexene mL | 1-Hexene mol/L | Time min | Yield g | Activity g/mol/h | MFR g/10 min | FR | Mw $10^{-4}$ | Mw/Mn — | Tm ° C. | d g/cm$^3$ |
|---|---|---|---|---|---|---|---|---|---|---|---|---|
| Example 32 | 683 | 17 | 0.2 | 60 | 26.9 | 1.1E+05 | 0.12 | 6.27 | 20.4 | 2.0 | 132.7 | 0.9347 |
| Example 33 | 603 | 87 | 1.0 | 120 | 33.9 | 6.8E+05 | 0.17 | 6.45 | 17.6 | 2.2 | 127.6 | 0.9267 |

Conditions: Pd(dba)2/Ligand = 1; Catalyst, 25 μmol; Ethylene, 3 MPa; 80° C.

(17) [Example 34: copolymerization of ethylene/propylene]

Copolymerization was performed in the same manner as in Example 23 except for not using methyl acrylate and using 700 mL of purified toluene. As a result, 36 g of a ethylene/propylene copolymer was recovered. The catalytic activity was 4.3E+05 g/mol/h. The molecular weight Mw of the obtained copolymer was 23,000, Mw/Mn was 2.3, the melting point was 90.2° C., and the propylene content was 16.9 mol.

(18) [Example 35: polymerization of propylene]

Methylene chloride slurries (0.02 mol/L) of bis(benzylideneacetone)palladium and Phosphorus-Sulfonic Acid Ligand (I) were separately prepared and after treatment by an ultrasonic vibrator, mixed in a molar ratio of 1:1, and the mixture was stirred at room temperature for 15 minutes. Subsequently, the 10 mL stainless autoclave reactor was purged with purified nitrogen, and purified toluene was introduced. After raising the temperature to 80° C. and pressurizing the system with propylene to 0.5 MPa, 8 μmol of the catalyst slurry prepared above was added, and polymerization was started. Here, the total liquid amount was adjusted to become 5 mL during the polymerization. The temperature was kept constant during the reaction, and propylene was continuously supplied so that the partial pressure of propylene could be kept at 0.5 MPa. After 60 minutes, the unreacted propylene was purged, and the autoclave was cooled to room temperature. The entire amount of the solvent was removed by evaporation, and the polymer was dried under reduced pressure at 40° C. for 6 hours and recovered. The catalytic activity was 4.75E+03 g/mol/h. The molecular weight Mw of the obtained polymer was 136,000 in terms of polyethylene, and Mw/Mn was 2.7.

(19) [Example 36: copolymerization of propylene/methyl acrylate]

Methylene chloride slurries (0.02 mol/L) of bis(benzylideneacetone)palladium and Phosphorus-Sulfonic Acid Ligand (I) were separately prepared and after treatment by an ultrasonic vibrator, mixed in a molar ratio of 1:1, and the mixture was stirred at room temperature for 15 minutes. Subsequently, the 10 mL stainless autoclave reactor was purged with purified nitrogen, and purified toluene and methyl acrylate (6 mmol) were introduced. After raising the temperature to 80° C. and pressurizing the system with propylene to 0.5 MPa, 8 μmol of the catalyst slurry prepared above was added, and polymerization was started. Here, the total liquid amount was adjusted to become 5 mL during the polymerization. The temperature was kept constant during the reaction, and propylene was continuously supplied so that the partial pressure of propylene could be kept at 0.5 MPa. After 60 minutes, the unreacted propylene was purged, and the autoclave was cooled to room temperature. The entire amount of the solvent was removed by evaporation, and the polymer was dried under reduced pressure at 40° C. for 6 hours and recovered. The catalytic activity was 3.90E+03 g/mol/h. The molecular weight Mw of the obtained polymer was 194,000 in terms of polyethylene, and Mw/Mn was 2.0.

(20) [comparative example 35]

For comparison, evaluations of commercially available metallocene polyethylene and high pressure-process ethyl acrylate copolymer were performed by the same method as in Examples above. The polymers used were metallocene LL "KARNEL" KF370 produced by Japan Polyethylene Corp. in Comparative Example 35-1, KF373N of the same product in Comparative Example 35-2, KF480 of the same product in Comparative Example 35-3, high pressure-process EEA "REXPEARL EEA" A1100 produced by Japan Polyethylene Corp. in Comparative Example 35-4, and A1200 of the same product in Comparative Example 35-5. Incidentally, in Comparative Examples 35-4 and 35-5, the copolymer at the polymerization is only ethyl acrylate but since the polymer has methyl, ethyl, butyl and amyl branches which are unavoidably by-produced, the total of these short-chain branches was converted into the short-chain branch concentration [C] based on the main-chain carbon and used for comparison. The results are shown together in Table 16.

TABLE 16

| | | MFR g/10 min | Density g/cm³ | Mw | Mw/Mn | Tm °C. | By-Produced Short-Chain Branch branches/1000C | [C] mol % | [X] mol % | [C] + [X] mol % |
|---|---|---|---|---|---|---|---|---|---|---|
| Comp. Example 35-1 | KERNEL KF370 | 3.5 | 0.905 | 84,000 | 2.1 | 88.0 | — | 5.8 | 0.0 | 5.8 |
| Comp. Example 35-2 | KERNEL KF373N | 3.5 | 0.913 | 84,000 | 2.1 | 98.5 | — | 4.8 | 0.0 | 4.8 |
| Comp. Example 35-3 | KERNEL KF480 | 4.0 | 0.918 | 74,000 | 2.7 | 106.7 | — | 3.8 | 0.0 | 3.8 |
| Comp. Example 35-4 | REXPEARL EEA A1100 | 0.4 | 0.929 | 84,000 | 3.4 | 101.2 | 9.5 | 1.9 | 3.8 | 5.7 |
| Comp. Example 35-5 | REXPEARL EEA A1200 | 0.7 | 0.935 | 94,000 | 3.5 | 94.1 | 10.0 | 2.0 | 6.9 | 8.9 |

(21) Evaluation Results of Physical Properties

Evaluation results of physical properties of obtained samples are shown in Table 17.

TABLE 17

| | Item 1 Mw | Item 2 Mw/Mn | Item 3 Tm °C. | Item 4 [C] + [X] Mol % | Item 5 135 − 6.4 × ([C] + [X]) | Item 6 $\delta(G^* = 10^5)$ ° | Item 7 T90 − T10 °C. | Item 8 Tw °C. | Item 9 28 − 0.3*Tw °C. | Item 10 41 − 0.3*Tw °C. |
|---|---|---|---|---|---|---|---|---|---|---|
| Example 12 | 92,000 | 2.1 | 102.9 | 3.7 | 112.9 | 66.2 | 10.7 | 67.9 | 7.6 | 20.6 |
| Example 13 | 125,000 | 1.8 | 111.2 | 2.1 | 122.5 | 71.7 | 7.4 | 78.4 | 4.5 | 17.5 |
| Example 14 | 86,000 | 2.0 | 95.7 | 4.8 | 104.3 | 68.3 | 15.9 | 56.0 | 11.2 | 24.2 |
| Example 15 | 84,000 | 2.0 | 96.0 | 4.6 | 105.6 | 68.2 | 14.9 | 56.8 | 11.0 | 24.0 |
| Example 16 | 142,000 | 1.9 | 112.4 | 1.9 | 122.8 | 68.0 | 7.2 | 80.9 | 3.7 | 16.7 |
| Example 17 | 72,900 | 1.8 | 110.0 | 2.4 | 119.6 | 69.7 | 12.9 | 74.9 | 5.5 | 18.5 |
| Example 18 | 71,900 | 1.8 | 106.1 | 2.9 | 116.4 | 68.7 | 13.4 | 70.1 | 7.0 | 20.0 |
| Example 19 | 76,200 | 1.9 | 110.7 | 2.4 | 119.6 | 68.3 | 10.8 | 75.7 | 5.3 | 18.3 |
| Example 20 | 165,000 | 2.7 | 117.6 | 1.3 | 126.7 | 46.9 | 11.3 | 85.6 | 2.3 | 15.3 |
| Example 21 | 120,600 | 2.1 | 105.2 | 3.1 | 115.2 | 62.9 | 16.9 | 68.9 | 7.3 | 20.3 |
| Example 22 | 111,100 | 2.0 | 104.5 | 3.4 | 113.2 | 65.9 | 19.8 | 66.8 | 8.0 | 21.0 |
| Example 23 | 65,000 | 1.9 | 92.1 | 6.1 | 96.0 | | | | | |
| Example 24 | 80,000 | 1.7 | 107.2 | 4.0 | 109.4 | 72.9 | 11.3 | 71.1 | 6.7 | 19.7 |
| Example 25 | 58,000 | 1.6 | 113.6 | 3.0 | 115.8 | 71.3 | 12.5 | 77.2 | 4.8 | 17.8 |
| Example 26 | 55,000 | 1.9 | 120.1 | 1.6 | 124.8 | | 7.8 | 84.8 | 2.6 | 15.6 |
| Example 27 | 174,000 | 2.4 | 135.1 | | 135.0 | | | | | |
| Example 30 | 131,000 | 2.1 | 110.2 | 2.5 | 119.0 | | 9.5 | 76.2 | 5.1 | 18.1 |
| Example 31 | 134,000 | 2.1 | 118.8 | 1.3 | 126.7 | 62.5 | 12.8 | 85.8 | 2.3 | 15.3 |
| Example 32 | 204,000 | 2.0 | 132.7 | 0.1 | 134.4 | 67.2 | 2.3 | 97.7 | −1.3 | 11.7 |
| Example 33 | 176,000 | 2.2 | 127.6 | 0.4 | 132.4 | 51.0 | 2.5 | 93.9 | −0.2 | 12.8 |
| Example 34 | 23,000 | 2.3 | 90.2 | 16.9 | 26.8 | | | | | |
| Comparative Example 35-1 | 84,000 | 2.1 | 88.0 | 5.8 | 98.1 | 63.2 | 18.1 | 59.3 | 10.2 | 23.2 |
| Comparative Example 35-2 | 84,000 | 2.1 | 98.5 | 4.8 | 104.2 | 63.5 | 16.9 | 61.3 | 9.6 | 22.6 |
| Comparative Example 35-3 | 74,000 | 2.7 | 106.7 | 3.8 | 110.8 | 64.6 | 13.2 | 76.5 | 5.1 | 18.1 |
| Comparative Example 35-4 | 84,000 | 3.4 | 101.2 | 5.7 | 98.8 | 34.4 | 33.6 | 60.6 | 9.8 | 22.8 |
| Comparative Example 35-5 | 94,000 | 3.5 | 94.1 | 8.9 | 78.0 | 35.3 | 34.8 | 49.6 | 13.1 | 28.1 |

| | Item 11 Tensile Modulus MPa | Item 12 Tensile Yield Stress MPa | Item 13 Nominal Tensile Stress at Break MPa | Item 14 nominal tensile strain at break | Item 16 Tensile impact strength kJ/m² | Item 17 Wettability | 18 Remarks |
|---|---|---|---|---|---|---|---|
| Example 12 | 106 | 8.9 | 33.5 | 13.5 | 2046 | B | As a result of 13C-NMR |
| Example 13 | 136 | 11.4 | 43.5 | 12.3 | 2353 | B | measurement (lower |
| Example 14 | 35 | 6.9 | 40.7 | 15.2 | 1947 | A | detection limit: 0.1 |
| Example 15 | 40 | 7.2 | 37.7 | 14.9 | 1768 | A | branches/1,000 carbon), no |
| Example 16 | 142 | 12.2 | 46.6 | 13.1 | 2261 | C | branch was detected except |
| Example 17 | 138 | 11.6 | 33.2 | 13.1 | 1280 | C | for branch structures |
| Example 18 | 113 | 10.0 | 32.8 | 13.9 | 1264 | C | derived from α-olefin and |
| Example 19 | 158 | 11.9 | 30.7 | 11.2 | 1236 | C | ((meth)acrylic acid)-based |

TABLE 17-continued

| | | | | | | | |
|---|---|---|---|---|---|---|---|
| Example 20 | 277 | 15.0 | 43.5 | 13.3 | 1544 | C | olefin which are the |
| Example 21 | 90 | 9.1 | 45.5 | 14.1 | 2286 | B | comonomer. Also, a |
| Example 22 | 69 | 8.8 | 46.3 | | 2147 | B | ((meth)acrylic acid)-based |
| Example 23 | | | | | | | olefin present in the |
| Example 24 | 131 | 11.6 | | | | B | terminal of molecular chain |
| Example 25 | 243 | 15.4 | | | | C | was not detected. |
| Example 26 | | | | | | | Furthermore, a chain |
| Example 27 | | | | | | | structure where two or more |
| Example 30 | | | | | | | units of α-olefin or |
| Example 31 | | | | | | | ((meth)acrylic acid)-based |
| Example 32 | | | | | | | olefin are continuously |
| Example 33 | | | | | | | connected was not detected. |
| Example 34 | | | | | | | |
| Comparative Example 35-1 | 57 | 7.8 | 39.5 | 13.8 | 2999 | D | |
| Comparative Example 35-2 | 91 | 9.4 | 40.1 | 13.6 | 2477 | D | |
| Comparative Example 35-3 | 118 | 11.2 | 41.3 | 14.8 | 1671 | D | |
| Comparative Example 35-4 | 99 | 8.1 | 27.2 | 14.4 | 990 | A | |
| Comparative Example 35-5 | 33 | 5.3 | 19.0 | 14.3 | 932 | A | |

5. Review Results of Examples and Comparative Examples

Example 1 revealed that by using the catalyst composition according to the present invention, relatively high activity and good balance of both the comonomer content and the molecular weight can be expressed.

Example 2 revealed that in contrast to the related art where an ethylene-acrylate copolymer cannot be obtained, the copolymer can be produced by using the nickel complex according to the present invention for the catalyst.

Example 3 revealed that by using the catalyst composition according to the present invention, relatively high activity and good balance of both the comonomer content and the molecular weight compared with Comparative Examples which are the related art, can be expressed.

Example 4 revealed that by using the catalyst composition according to the present invention, various comonomers can be made applicable.

Example 5 revealed that by using the phosphorus-sulfonic acid ligand according to the present invention in combination with nickel for a catalyst composition, an ethylene/polar group-containing olefin copolymer can be produced.

Example 6 revealed that even when the phosphorus-sulfonic acid ligand according to the present invention is used in combination with nickel for a catalyst composition and aniline, MMA, clay or triphenylborane is added as the third component, an ethylene/polar group-containing olefin copolymer can be produced.

Example 7 revealed that by using the phosphorus-sulfonic acid ligand according to the present invention in combination with nickel for a catalyst composition, an ethylene homopolymer can be produced with high activity.

Examples 8 and 9 revealed that even when a catalyst carrying the phosphorus-sulfonic acid ligand according to the present invention and palladium is used, an ethylene polymer and an ethylene-acrylate copolymer are obtained.

Examples 10 and 11 revealed that even when a catalyst carrying the phosphorus-sulfonic acid ligand according to the present invention and nickel is used, an ethylene polymer can be obtained with higher activity than in Comparative Examples which are the related art. It is also revealed that an ethylene-acrylate copolymer is obtained.

Examples 12 to 22 revealed that thanks to the reaction product of the phosphorus-sulfonic acid ligand and a palladium compound, which is the catalyst composition of the present invention, an ethylene-1-hexene-acrylate ternary copolymer having a narrow molecular weight distribution and a relatively high molecular weight can be produced. Furthermore, Examples 23 to 26 revealed that an ethylene-propylene-methyl acrylate ternary copolymer can be also produced.

Examples 27 to 29 revealed that thanks to the reaction product of the phosphorus-sulfonic acid ligand and a palladium compound, which is the catalyst composition of the present invention, an ethylene homopolymer can be produced with high activity and the obtained polymer can have a high molecular weight and a narrow molecular weight distribution, that is, a polymer with little difference in branching can be produced.

In Examples 30 to 33, it was confirmed that thanks to the reaction product of the phosphorus-sulfonic acid ligand and a palladium compound, which is the catalyst composition of the present invention, similarly to Example-1 and Example 4, copolymerization between ethylene and acrylate or between ethylene and 1-hexene proceeds.

In Example 34, it was confirmed by $^{13}$C-NMR that thanks to the reaction product of the phosphorus-sulfonic acid ligand and a palladium compound, which is the catalyst composition of the present invention, copolymerization between ethylene and propylene proceeds.

Examples 35 and 36 revealed that thanks to the reaction product of the phosphorus-sulfonic acid ligand and a palladium compound, which is the catalyst composition of the present invention, propylene homopolymerization and copolymerization of propylene/methyl acrylate proceed.

As a result of physical evaluations, the polymer of Example 14 has almost the same elastic modulus and almost the same molecular weight as the polymer of Comparative Example 35-5, but when these two polymers are compared, the wettability is almost the same, whereas as for the mechanical properties, all of the tensile yield stress, nominal tensile stress at break, nominal tensile strain at break and tensile impact strength in Example 14 show a higher value than in Comparative Example 35-5 and are excellent.

The polymer of Example 18 has almost the same elastic modulus and almost the same molecular weight as the polymer of Comparative Example 35-3, but when these two polymers are compared, the mechanical properties are almost the same in all of the tensile yield stress, nominal tensile stress at break and nominal tensile strain at break and while the tensile impact strength shows a relatively high value in Comparative Example 35-3 and is excellent, the wettability is more excellent in Example 18 than Comparative Example 35-3. Accordingly, the polymer of Example 18 can be said to have a good balance between the mechanical properties and the wettability.

While the invention has been described in detail and with reference to specific embodiments thereof, it will be apparent to one skilled in the art that various changes and modifications can be made therein without departing from the spirit and scope of the invention.

This application is based on Japanese Patent Application (Patent Application No. 2008-297411) filed on Nov. 20, 2008, and Japanese Patent Application (Patent Application No. 2009-025443) filed on Feb. 5, 2009, the contents of which are incorporated herein by way of reference.

INDUSTRIAL APPLICABILITY

By performing copolymerization of an α-olefin in the presence of the catalyst composition of the present invention, an industrially useful copolymer having a high comonomer content and at the same time, having a high molecular can be produced. This copolymer is excellent in the mechanical and thermal properties and applicable as a useful formed body. More specifically, the copolymer of the present invention can be applied to various uses such as film, sheet, adhesive resin, binder and compatibilizer, by utilizing its good properties in terms of, for example, coatability, printability, antistatic property, inorganic filler dispersibility, adhesion to other resins, and compatibilizing ability for other resins.

The invention claimed is:

1. A metal complex represented by the following formula (2):

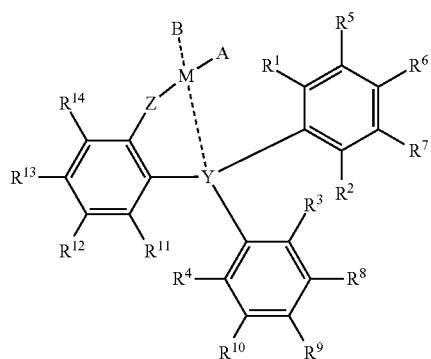

wherein Y is phosphorus or arsenic, Z is —$SO_3$— or $CO_2$—, wherein $R^1$ is a hydrogen atom, $R^2$ is a secondary alkyl group having from 3 to 6 carbon atoms, $R^3$ is a hydrogen atom, and $R^4$ is a secondary alkyl group having from 3 to 6 carbon atoms, each of $R^5$ to $R^{14}$ independently represents a hydrogen atom, a halogen atom, or a hydrocarbon group having a carbon number of 1 to 30, which may have a heteroatom, M represents a metal atom selected from the group consisting of transition metals of Groups 8 to 10 of the periodic table, A represents a hydrogen atom, an alkyl group having a carbon number of 1 to 30, which may have a heteroatom, or an aryl group having a carbon number of 6 to 30, which may have a heteroatom, B represents an arbitrary ligand coordinated to M, and A and B may combine with each other to form a ring.

2. An α-olefin polymerization catalyst comprising the metal complex claimed in claim 1.

3. An α-olefin polymerization catalyst comprising the metal complex claimed in claim 1 and a fine particle support.

4. The α-olefin polymerization catalyst as claimed in claim 3, wherein the fine particle support is an ion-exchanging layered silicate.

5. The α-olefin polymerization catalyst as claimed in claim 4, wherein the ion-exchanging layered silicate belongs to a smectite group.

6. A process for producing an α-olefin.((meth)acrylic acid)-based copolymer, comprising copolymerizing an α-olefin and a (meth)acrylic acid or ester in the presence of the α-olefin polymerization catalyst claimed in any one of claims 2 or 3.

7. A process for producing an α-olefin.(meth)acrylic acid)-based copolymer, comprising copolymerizing three components: two different α-olefins; and a (meth)acrylic acid or ester, in the presence of the α-olefin polymerization catalyst claimed in any one of claims 2 or 3.

* * * * *